US012561955B2

(12) United States Patent
Watanabe

(10) Patent No.: US 12,561,955 B2
(45) Date of Patent: Feb. 24, 2026

(54) ENDOSCOPE SYSTEM AND METHOD OF OPERATING THE SAME

(71) Applicant: FUJIFILM Corporation, Tokyo (JP)

(72) Inventor: Hiroki Watanabe, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 18/474,252

(22) Filed: Sep. 26, 2023

(65) Prior Publication Data

US 2024/0029404 A1     Jan. 25, 2024

Related U.S. Application Data

(63) Continuation of application No. PCT/JP2022/006397, filed on Feb. 17, 2022.

(30) Foreign Application Priority Data

Mar. 31, 2021     (JP) ................................. 2021-060899

(51) Int. Cl.
*G06V 10/764*     (2022.01)
*A61B 1/00*     (2006.01)
*A61B 1/045*     (2006.01)
*A61B 1/06*     (2006.01)

(52) U.S. Cl.
CPC ...... *G06V 10/764* (2022.01); *A61B 1/000094* (2022.02); *A61B 1/00048* (2013.01); *A61B 1/045* (2013.01); *A61B 1/0638* (2013.01); *G06V 2201/03* (2022.01)

(58) Field of Classification Search
CPC ............. G06V 10/764; G06V 2201/03; G06V 10/141; G06V 10/143; G06V 10/25; G06V 10/56; G06V 10/50; A61B 1/000094; A61B 1/00048; A61B 1/045; A61B 1/0638;
(Continued)

(56) References Cited

U.S. PATENT DOCUMENTS

| 8,184,146 B2 | 5/2012 | Tanaka et al. |
| 11,950,762 B2 | 4/2024 | Koizumi et al. |
| 12,039,736 B2 | 7/2024 | Tsukatani et al. |

(Continued)

FOREIGN PATENT DOCUMENTS

| EP | 2727514 | 5/2014 |
| EP | 3701852 | 9/2020 |

(Continued)

OTHER PUBLICATIONS

"Search Report of Europe Counterpart Application", issued on Jul. 17, 2024, p. 1-p. 115.

(Continued)

*Primary Examiner* — Nasim N Nirjhar
(74) *Attorney, Agent, or Firm* — JCIPRNET

(57) ABSTRACT

An endoscope system that illuminates a subject and captures light from the subject acquires an examination image based on an image signal captured by an endoscope, divides the examination image into a plurality of regions as an input image, inputs the input image divided into the plurality of regions to a first classifier to output region evaluation values for the plurality of regions, and inputs an input image in which the region evaluation values are added to the plurality of regions to a second classifier to output a lesion evaluation value.

16 Claims, 24 Drawing Sheets

FIRST SCREEN (DISPLAY IMAGE)     SECOND SCREEN (LESION EVALUATION VALUE)

| 0.01 | 0.05 | 0.01 | 0.01 |
| 0.01 | 0.02 | 0.2 | 0.01 |
| 0.01 | 0.2 | 0.95 | 0.01 |
| 0.7 | 0.01 | 0.01 | 0.01 |

180

182

17a     17b

(58) Field of Classification Search

CPC . A61B 1/000096; A61B 1/0005; A61B 1/044;
A61B 1/0655; A61B 3/0058; G06T
7/0012

See application file for complete search history.

(56) References Cited

U.S. PATENT DOCUMENTS

| | | | |
|---|---|---|---|
| 2011/0280443 A1 | 11/2011 | Kitamura et al. | |
| 2018/0114319 A1* | 4/2018 | Kono | A61B 1/018 |
| 2019/0192048 A1* | 6/2019 | Makino | A61B 1/0638 |
| 2020/0242764 A1 | 7/2020 | Aoyama | |
| 2021/0019580 A1* | 1/2021 | Sakane | G06V 30/1916 |
| 2021/0169306 A1 | 6/2021 | Oosake | |
| 2021/0264592 A1 | 8/2021 | Aoyama | |
| 2021/0321856 A1 | 10/2021 | Koizumi et al. | |
| 2022/0020147 A1 | 1/2022 | Sasada et al. | |
| 2023/0100147 A1* | 3/2023 | Kubota | G06V 10/764 |
| | | | 382/128 |
| 2023/0119040 A1 | 4/2023 | Aoyama | |

FOREIGN PATENT DOCUMENTS

| | | | | |
|---|---|---|---|---|
| JP | 2011024628 | 2/2011 | | |
| JP | 2011218090 | 11/2011 | | |
| JP | 2011239843 | 12/2011 | | |
| WO | 2007119295 | 10/2007 | | |
| WO | WO-2019039354 A1 * | 2/2019 | ......... | A61B 1/00009 |
| WO | 2019078204 | 4/2019 | | |
| WO | 2020040059 | 2/2020 | | |
| WO | 2020066670 | 4/2020 | | |
| WO | 2020100630 | 5/2020 | | |
| WO | 2020121906 | 6/2020 | | |
| WO | 2020121996 | 6/2020 | | |
| WO | 2020218029 | 10/2020 | | |

OTHER PUBLICATIONS

"International Search Report (Form PCT/ISA/210) of PCT/JP2022/006397," mailed on Apr. 12, 2022, with English translation thereof, pp. 1-7.

"Written Opinion of the International Searching Authority (Form PCT/ISA/237) of PCT/JP2022/006397," mailed on Apr. 12, 2022, with English translation thereof, pp. 1-10.

"Notice of Reasons for Refusal of Japan Counterpart Application", issued on Sep. 2, 2025, with English translation thereof, p. 1-p. 13.

"Notice of Reasons for Refusal of Japan Counterpart Application", issued on Nov. 25, 2025, with English translation thereof, p. 1-p. 12.

* cited by examiner

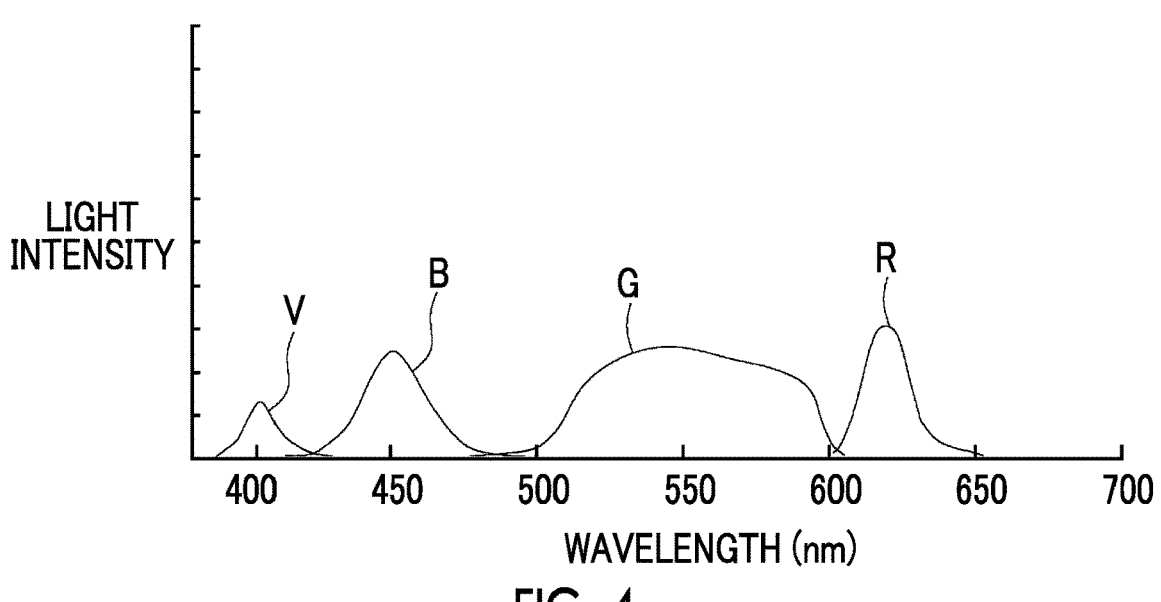

LIGHT INTENSITY

V    B    G    R

WAVELENGTH (nm)

| FIRST ILLUMINATION PERIOD | | SECOND ILLUMINATION PERIOD | FIRST ILLUMINATION PERIOD | | SECOND ILLUMINATION PERIOD |
|---|---|---|---|---|---|
| ONE FRAME | ONE FRAME | ONE FRAME | ONE FRAME | ONE FRAME | ONE FRAME |
| FIRST ILLUMINATION LIGHT (WHITE LIGHT) | FIRST ILLUMINATION LIGHT (WHITE LIGHT) | SECOND ILLUMINATION LIGHT | FIRST ILLUMINATION LIGHT (WHITE LIGHT) | FIRST ILLUMINATION LIGHT (WHITE LIGHT) | SECOND ILLUMINATION LIGHT |

SAME EMISSION SPECTRUM time

FIG. 5

| FIRST ILLUMINATION PERIOD | | SECOND ILLUMINATION PERIOD | FIRST ILLUMINATION PERIOD | | | SECOND ILLUMINATION PERIOD |
|---|---|---|---|---|---|---|
| ONE FRAME | ONE FRAME | ONE FRAME | ONE FRAME | ONE FRAME | ONE FRAME | ONE FRAME |
| FIRST ILLUMINATION LIGHT (WHITE LIGHT) | FIRST ILLUMINATION LIGHT (WHITE LIGHT) | SECOND ILLUMINATION PERIOD | FIRST ILLUMINATION LIGHT (WHITE LIGHT) | FIRST ILLUMINATION LIGHT (WHITE LIGHT) | FIRST ILLUMINATION LIGHT (WHITE LIGHT) | SECOND ILLUMINATION PERIOD | time

FIG. 6

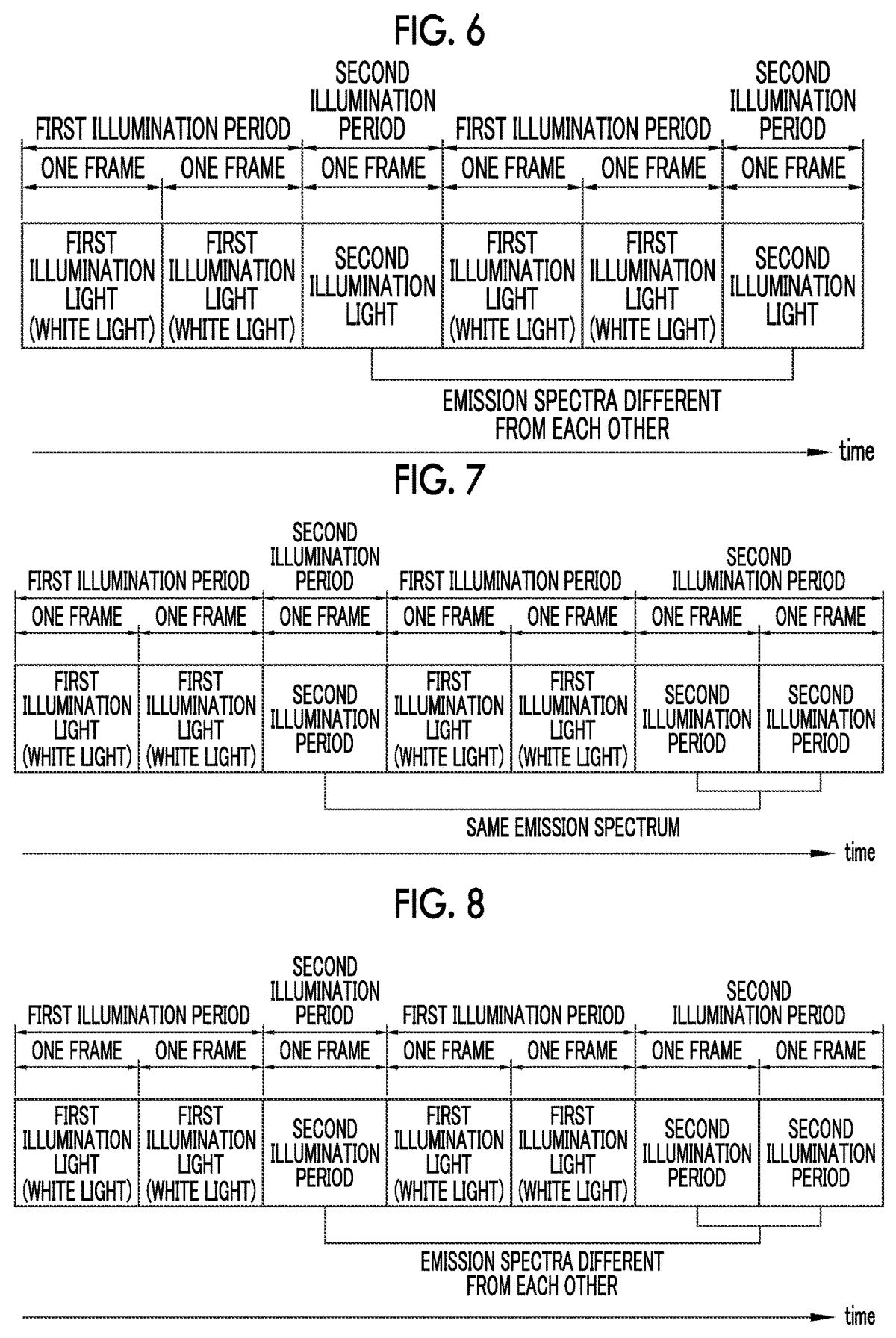

| FIRST ILLUMINATION PERIOD | | SECOND ILLUMINATION PERIOD | FIRST ILLUMINATION PERIOD | | SECOND ILLUMINATION PERIOD |
|---|---|---|---|---|---|
| ONE FRAME | ONE FRAME | ONE FRAME | ONE FRAME | ONE FRAME | ONE FRAME |
| FIRST ILLUMINATION LIGHT (WHITE LIGHT) | FIRST ILLUMINATION LIGHT (WHITE LIGHT) | SECOND ILLUMINATION LIGHT | FIRST ILLUMINATION LIGHT (WHITE LIGHT) | FIRST ILLUMINATION LIGHT (WHITE LIGHT) | SECOND ILLUMINATION LIGHT |

EMISSION SPECTRA DIFFERENT
FROM EACH OTHER

→ time

FIG. 7

| FIRST ILLUMINATION PERIOD | | SECOND ILLUMINATION PERIOD | FIRST ILLUMINATION PERIOD | | SECOND ILLUMINATION PERIOD | |
|---|---|---|---|---|---|---|
| ONE FRAME | ONE FRAME | ONE FRAME | ONE FRAME | ONE FRAME | ONE FRAME | ONE FRAME |
| FIRST ILLUMINATION LIGHT (WHITE LIGHT) | FIRST ILLUMINATION LIGHT (WHITE LIGHT) | SECOND ILLUMINATION PERIOD | FIRST ILLUMINATION LIGHT (WHITE LIGHT) | FIRST ILLUMINATION LIGHT (WHITE LIGHT) | SECOND ILLUMINATION PERIOD | SECOND ILLUMINATION PERIOD |

SAME EMISSION SPECTRUM

→ time

FIG. 8

| FIRST ILLUMINATION PERIOD | | SECOND ILLUMINATION PERIOD | FIRST ILLUMINATION PERIOD | | SECOND ILLUMINATION PERIOD | |
|---|---|---|---|---|---|---|
| ONE FRAME | ONE FRAME | ONE FRAME | ONE FRAME | ONE FRAME | ONE FRAME | ONE FRAME |
| FIRST ILLUMINATION LIGHT (WHITE LIGHT) | FIRST ILLUMINATION LIGHT (WHITE LIGHT) | SECOND ILLUMINATION PERIOD | FIRST ILLUMINATION LIGHT (WHITE LIGHT) | FIRST ILLUMINATION LIGHT (WHITE LIGHT) | SECOND ILLUMINATION PERIOD | SECOND ILLUMINATION PERIOD |

EMISSION SPECTRA DIFFERENT
FROM EACH OTHER

→ time

FIG. 9

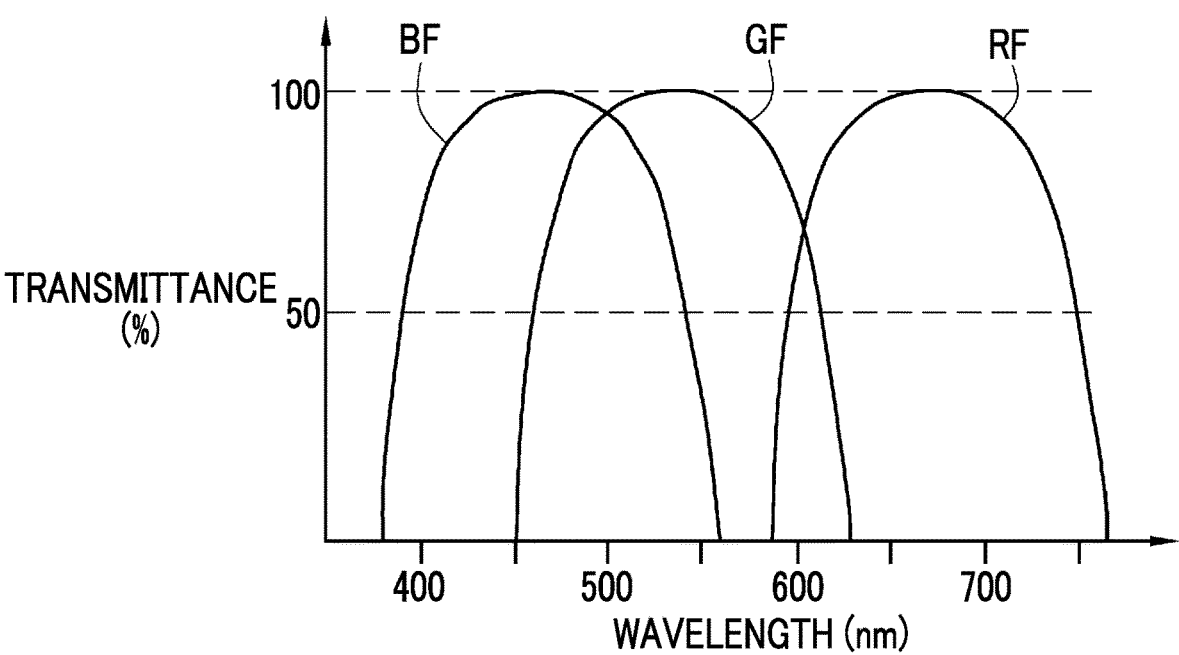

FIG. 10

| | FIRST ILLUMINATION PERIOD | | SECOND ILLUMINATION PERIOD | FIRST ILLUMINATION PERIOD | | SECOND ILLUMINATION PERIOD |
|---|---|---|---|---|---|---|
| | ONE FRAME | ONE FRAME | ONE FRAME | ONE FRAME | ONE FRAME | ONE FRAME |
| EMISSION PATTERN | FIRST ILLUMINATION LIGHT (WHITE LIGHT) | FIRST ILLUMINATION LIGHT (WHITE LIGHT) | SECOND ILLUMINATION PERIOD | FIRST ILLUMINATION LIGHT (WHITE LIGHT) | FIRST ILLUMINATION LIGHT (WHITE LIGHT) | SECOND ILLUMINATION PERIOD |
| | FIRST IMAGING PERIOD | | SECOND ILLUMINATION PERIOD | FIRST IMAGING PERIOD | | SECOND ILLUMINATION PERIOD |
| IMAGING PATTERN | FIRST IMAGE SIGNAL | FIRST IMAGE SIGNAL | SECOND IMAGE SIGNAL | FIRST IMAGE SIGNAL | FIRST IMAGE SIGNAL | SECOND IMAGE SIGNAL | time

| REGION A | REGION B | REGION C | REGION D |
|---|---|---|---|
| REGION E | REGION F | REGION G | REGION H |
| REGION I | REGION J | REGION K | REGION L |
| REGION M | REGION N | REGION O | REGION P |

EXTRACTION REGION

FIG. 28

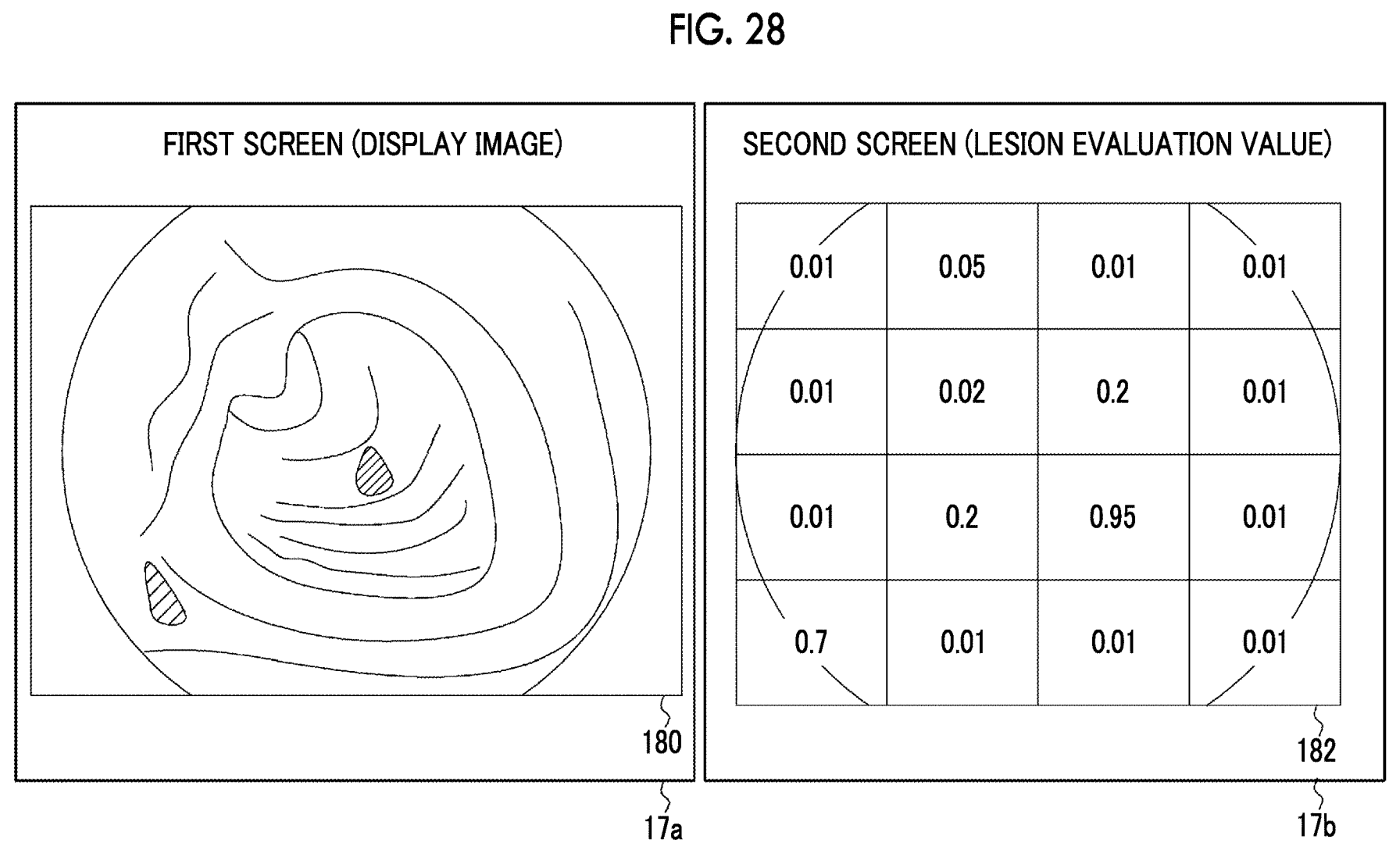

SECOND SCREEN (LESION EVALUATION VALUE)

| | | | |
|---|---|---|---|
| 0.01 | 0.01 | 0.01 | 0.01 |
| 0.01 | 0.2 | 0.95 | 0.01 |
| 0.05 | 0.02 | 0.2 | 0.01 |
| 0.01 | 0.01 | 0.01 | 0.7 |

182

17b

FIRST SCREEN (DISPLAY IMAGE)

ENDOSCOPE SYSTEM AND METHOD OF OPERATING THE SAME

CROSS-REFERENCE TO RELATED APPLICATIONS

This application is a Continuation of PCT International Application No. PCT/JP2022/006397 filed on 17 Feb. 2022, which claims priority under 35 U.S.C. § 119(a) to Japanese Patent Application No. 2021-060899 filed on 31 Mar. 2021. The above application is hereby expressly incorporated by reference, in its entirety, into the present application.

BACKGROUND OF THE INVENTION

1. Field of the Invention

The present invention relates to an endoscope system that performs an image analysis and a method of operating the same.

2. Description of the Related Art

In a current medical field, a medical image processing system using a medical image, such as an endoscope system comprising a light source device, an endoscope, and a processor device, is widely used.

In recent years, a region of interest having a possibility of a lesion area is extracted from a medical image, and an image analysis is performed on the extracted region of interest to acquire diagnostic information related to a disease state.

WO2020/121906A discloses a technique in which, in order to more accurately perform an image analysis on the region of interest, an image is divided and the divided image is evaluated for the region of interest.

SUMMARY OF THE INVENTION

In a medical image used for detection of a region of interest, in addition to the region of interest such as a lesion, a structure or an artifact that reduces an analysis accuracy other than the region of interest, such as a dark portion, blurriness, a residue, or a specular reflection may appear. The presence of such a structure or artifact interferes with the detection of the region of interest, and is one of factors that reduce the detection accuracy of the region of interest.

In a case where an evaluation value is calculated for an image with low evaluation suitability that includes a factor that reduces the detection accuracy, a reliability of an evaluation result will be low even in a case where the region of interest is included. Therefore, it is required to improve the detection accuracy of the region of interest by detecting the region of interest from the image after specifying the structure that causes a decrease in detection accuracy.

An object of the present invention is to provide an endoscope system and a method of operating the endoscope system that can detect a region of interest with a high reliability.

An endoscope system according to an aspect of the present invention illuminates a subject and captures light from the subject, and comprises an endoscope and an image control processor. The image control processor acquires an examination image based on an image signal captured by the endoscope, divides the examination image into a plurality of regions as an input image, inputs the input image divided into the plurality of regions to a first classifier to output region evaluation values for the plurality of regions, and inputs the input image in which the region evaluation values are added to the plurality of regions to a second classifier to output a lesion evaluation value.

It is preferable that the image control processor inputs the input image consisting of an extraction region extracted based on the region evaluation value among the plurality of regions to the second classifier to output the lesion evaluation value.

It is preferable that the region evaluation value is a value obtained by digitizing presence or absence of an evaluation inhibition target that is not suitable for outputting the lesion evaluation value on the input image and decreases an output accuracy of the lesion evaluation value and an influence of the evaluation inhibition target on the output of the lesion evaluation value.

It is preferable that the image control processor sets the plurality of regions in which the region evaluation value is equal to or greater than a threshold value as the extraction region. It is preferable that the plurality of regions in which the region evaluation value is less than the threshold value are regions including any one of a puddle, a blood pool, a liquid pool, a bubble, a distortion, blurriness, a reflection, or a cap.

It is preferable that the endoscope system further comprises a light source processor, the light source processor controls emission of first illumination light and second illumination light having emission spectra different from each other, and emits the first illumination light in a first emission pattern and emits the second illumination light in a second emission pattern in a case where a first illumination period during which the first illumination light is emitted and a second illumination period during which the second illumination light is emitted are automatically switched, and the image control processor sets a first illumination light image based on the first illumination light or a second illumination light image based on the second illumination light as the input image.

It is preferable that the image control processor sets the second illumination light image as the input image. It is preferable that the first illumination light is white light, and the second illumination light is light having a peak wavelength of 410 nm±10.

It is preferable that the endoscope system further comprises a display, the image control processor superimposes the lesion evaluation value output based on the second illumination light image acquired in a frame immediately before the first illumination light image is acquired as a numerical value or a color on the first illumination light image and displays a superimposed image on the display.

It is preferable that the image control processor performs any one of displaying the first illumination light image on a first screen of a first display and displaying the lesion evaluation value output based on the second illumination light image acquired in the frame immediately before the first illumination light image is acquired on a second screen of a second display in a case where the display comprises the first display and the second display different from each other, or displaying the first illumination light image on a first screen of a specific display and displaying the lesion evaluation value on a second screen of the specific display in a case where the display includes only one specific display.

It is preferable that the first emission pattern is any one of a first A emission pattern in which the number of frames of the first illumination period is the same in each of the first illumination periods or a first B emission pattern in which the number of frames of the first illumination period is different in each of the first illumination periods.

It is preferable that the second emission pattern is any one of a second A pattern in which the number of frames of the second illumination period is the same in each of the second illumination periods, and an emission spectrum of the second illumination light is the same in each of the second illumination periods, a second B pattern in which the number of frames of the second illumination period is the same in each of the second illumination periods, and an emission spectrum of the second illumination light is different in each of the second illumination periods, a second C pattern in which the number of frames of the second illumination period is different in each of the second illumination periods, and an emission spectrum of the second illumination light is the same in each of the second illumination periods, or a second D pattern in which the number of frames of the second illumination period is different in each of the second illumination periods, and an emission spectrum of the second illumination light is different in each of the second illumination periods.

It is preferable that the image control processor calculates an image evaluation value for the input image of any one frame using the lesion evaluation values for the plurality of regions output based on the input image of the one frame, calculates site evaluation values for the input images of a plurality of frames using the lesion evaluation values for the plurality of regions output based on the input images of the plurality of frames, and calculates an overall evaluation value using the image evaluation values and/or the site evaluation values added to the input images of all the frames to which the lesion evaluation values are output.

It is preferable that the image control processor determines a shape, a size, and/or the number of divisions of the input image based on a magnification at which the examination image is acquired. It is preferable that the lesion evaluation value is output based on an evaluation index for ulcerative colitis.

A method of operating an endoscope system according to another aspect of the present invention is provided with an endoscope that illuminates a subject and captures light from the subject and an image control processor, and comprises: via the image control processor, a step of acquiring an examination image based on an image signal captured by the endoscope; a step of dividing the examination image into a plurality of regions as an input image; a step of inputting the input image divided into the plurality of regions to a first classifier to output region evaluation values for the plurality of regions; and a step of inputting the input image in which the region evaluation values are added to the plurality of regions to a second classifier to output a lesion evaluation value.

An endoscope system according to still another aspect of the present invention is an endoscope system that illuminates a subject and captures light from the subject, the endoscope system comprising: an endoscope; and an image control processor, in which the image control processor acquires an examination image based on an image signal captured by the endoscope, inputs the examination image to a third classifier as an input image to output a removal image in which a specific region is removed from the input image, divides the removal image into a plurality of regions, and inputs the removal image divided into the plurality of regions to a second classifier to output a lesion evaluation value.

According to the aspects of the present invention, it is possible to provide an endoscope system and a method of operating the endoscope system that can detect a region of interest with a high reliability.

BRIEF DESCRIPTION OF THE DRAWINGS

FIG. 2 is a block diagram illustrating functions of the endoscope system.

FIG. 3 is a graph illustrating spectra of violet light V, blue light B, green light G, and red light R.

FIG. 4 is an explanatory diagram illustrating a first A emission pattern or a second A pattern in an enhancement observation mode.

FIG. 5 is an explanatory diagram illustrating a first B emission pattern in the enhancement observation mode.

FIG. 6 is an explanatory diagram illustrating a second B pattern in the enhancement observation mode.

FIG. 7 is an explanatory diagram illustrating a second C pattern in the enhancement observation mode.

FIG. 8 is an explanatory diagram illustrating a second D pattern in the enhancement observation mode.

FIG. 9 is a graph illustrating a spectroscopic transmittance of each color filter of an imaging sensor.

FIG. 10 is an explanatory diagram illustrating a first imaging period and a second imaging period.

FIG. 20 is an explanatory diagram illustrating an example of calculating a region evaluation value for each region of the divided input image.

FIG. 22 is an explanatory diagram illustrating a case where an extraction region is extracted.

FIG. 28 is an image diagram illustrating an example of a method of displaying a first screen and a second screen.

FIG. 29 is an image diagram illustrating an example in which the display image and the input image in which the lesion evaluation value is output for each region are displayed on a display screen.

DESCRIPTION OF THE PREFERRED EMBODIMENTS

Figure 1:
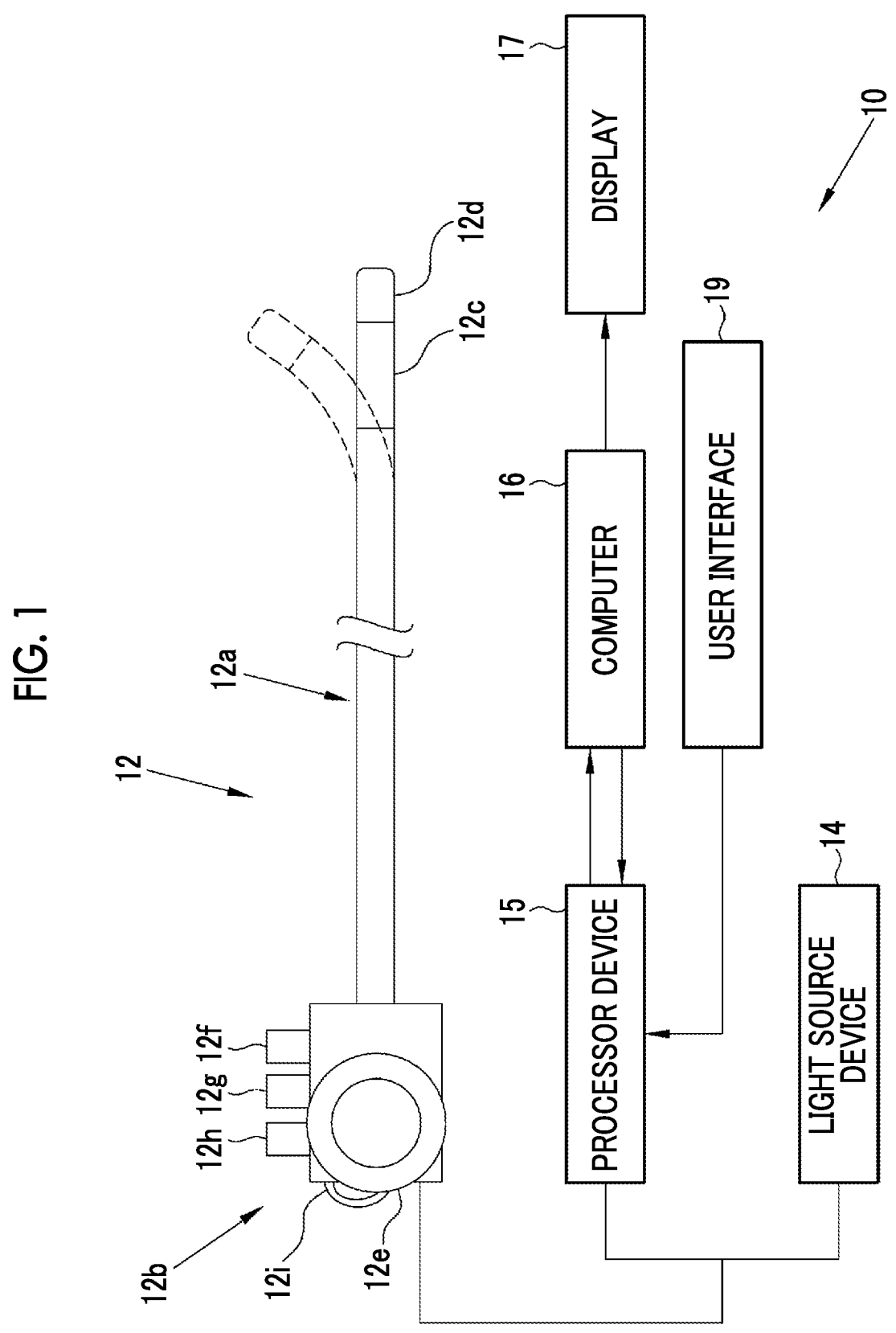
FIG. 1 is an explanatory diagram of a configuration of an endoscope system.

As illustrated in FIG. 1, an endoscope system 10 comprises an endoscope 12, a light source device 14, a processor device 15, a computer 16, a display 17, and a user interface 19. The endoscope 12 is optically connected to the light source device 14 and is electrically connected to the processor device 15. The endoscope 12 includes an insertion portion 12a to be inserted into a body of an observation target, an operation portion 12b provided at a proximal end portion of the insertion portion 12a, and a bendable portion 12c and a distal end portion 12d provided on a distal end side of the insertion portion 12a. The bendable portion 12c performs a bending operation by operating an angle knob 12e of the operation portion 12b. The distal end portion 12d is directed in a desired direction by the bending operation of the bendable portion 12c.

An optical system for forming a subject image and an optical system for irradiating the subject with illumination light are provided inside the endoscope 12. The operation portion 12b is provided with the angle knob 12e, an observation mode selector switch 12f, an image analysis mode selector switch 12g, a still image acquisition instruction switch 12h, and a zoom operation portion 12i. The observation mode selector switch 12f is used in an operation of switching observation modes. The still image acquisition instruction switch 12h is used for acquisition instruction for a still image of the observation target. The zoom operation portion 12i is used for operating a zoom lens 42.

The light source device 14 generates the illumination light. The display 17 outputs and displays an image of the observation target, information accompanying the image of the observation target, and the like. The user interface 19 includes a keyboard, a mouse, a touch pad, a microphone, and the like, and has a function of receiving an input operation such as function setting. The processor device 15 performs system control of the endoscope system 10, image processing on image signals transmitted from the endoscope 12, and the like.

The endoscope system 10 has three modes of a first illumination observation mode, a second illumination observation mode, and an image analysis mode, as observation modes. In a case where the observation mode selector switch 12f is pressed, the mode is switched through an image processing switching unit 54.

In the first illumination observation mode, the observation target is illuminated with normal light (first illumination light), such as white light, and imaging is performed to display a first illumination light image having a natural tone on the display 17. In the second illumination observation mode, the observation target is illuminated with special light (second illumination light) having a wavelength range different from that of the normal light, and imaging is performed to display a second illumination light image in which a specific structure is enhanced on the display 17. In the image analysis mode, the first illumination light and the second illumination light having different emission spectra are emitted while being switched. The image analysis mode is a mode in which the first illumination light image and/or the second illumination light image are analyzed, and an evaluation value for a region of interest having a possibility of a lesion area is output from the examination image and displayed.

Figure 2:
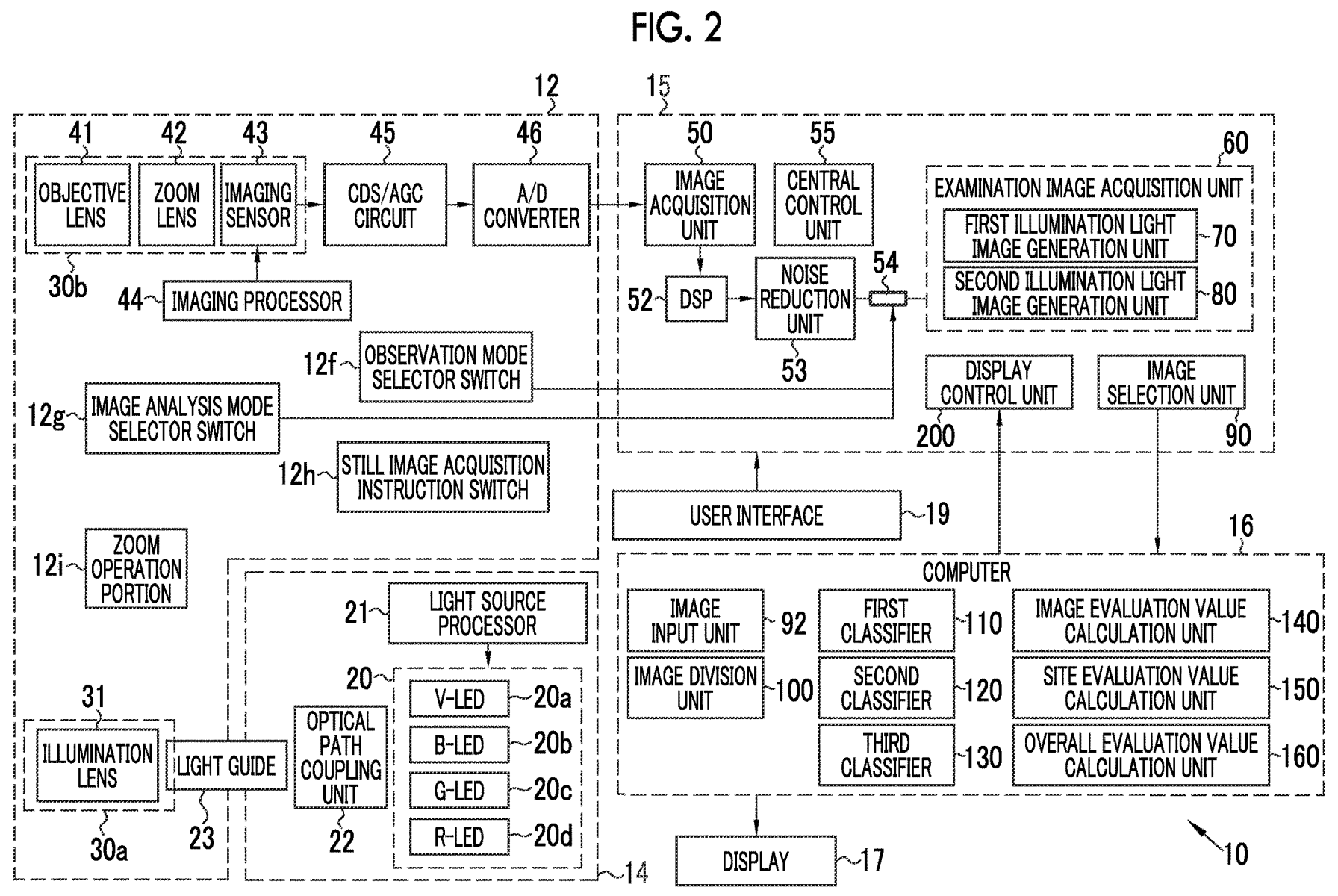

In FIG. 2, the light source device 14 comprises a light source unit 20 and a light source processor 21 that controls the light source unit 20. The light source unit 20 has, for example, a plurality of semiconductor light sources, turns on or off each of the semiconductor light sources, and in a case where the semiconductor light sources are turned on, controls a light emission quantity of each semiconductor light source to emit illumination light with which the observation target is illuminated. The light source unit 20 includes LEDs of four colors, that is, a violet light emitting diode (V-LED) 20a, a blue light emitting diode (B-LED) 20b, a green light emitting diode (G-LED) 20c, and a red light emitting diode (R-LED) 20d.

As illustrated in FIG. 3, the V-LED 20a generates violet light V having a central wavelength of 405±10 nm and a wavelength range of 380 to 420 nm. The B-LED 20b generates blue light B having a central wavelength of 450±10 nm and a wavelength range of 420 to 500 nm. The G-LED 20c generates green light G having a wavelength range of 480 to 600 nm. The R-LED 20d generates red light R having a central wavelength of 620 to 630 nm and a wavelength range of 600 to 650 nm.

The light source processor 21 controls the V-LED 20a, the B-LED 20b, the G-LED 20c, and the R-LED 20d. By controlling each of the LEDs 20a to 20d independently of each other, the light source processor 21 can emit the violet light V, the blue light B, the green light G, or the red light R by changing a light quantity independently of each other. In addition, in the first illumination observation mode, the light source processor 21 controls each of the LEDs to 20d such that white light for which a light quantity ratio among the violet light V, the blue light B, the green light G, and the red light R is Vc:Bc:Gc:Rc is emitted. Here, Vc, Bc, Gc, and Rc>0 is established.

In addition, in the second illumination observation mode, the light source processor 21 controls each of the LEDs 20a to 20d such that the special light for which the light quantity ratio among the violet light V, the blue light B, the green light G, and the red light R is Vs:Bs:Gs:Rs as narrow-band light having a short wavelength is emitted. The light quantity ratio Vs:Bs:Gs:Rs is different from the light quantity ratio Vc:Bc:Gc:Rc used in the first illumination observation mode and is appropriately determined according to an observation purpose.

Further, in a case where the first illumination light and the second illumination light are automatically switched and emitted in the image analysis mode, the light source processor 21 emits the first illumination light in a first emission pattern and emits the second illumination light in a second emission pattern. Specifically, it is preferable that the first emission pattern is any of a first A emission pattern in which the number of frames of a first illumination period is the same for each first illumination period as illustrated in FIG. 4, or a first B emission pattern in which the number of frames of the first illumination period is different for each first illumination period as illustrated in FIG. 5. In the figures, time represents a direction of the passage of time.

It is preferable that the second emission pattern is any one of a second A pattern in which the number of frames of a second illumination period is the same for each second illumination period and an emission spectrum of the second illumination light is the same for each second illumination period as illustrated in FIG. 4, a second B pattern in which the number of frames of the second illumination period is the same for each second illumination period and the emission spectrum of the second illumination light is different for each second illumination period as illustrated in FIG. 6, a second C pattern in which the number of frames of the second illumination period is different for each second illumination period and the emission spectrum of the second illumination light is the same for each second illumination period as illustrated in FIG. 7, or a second D pattern in which the number of frames of the second illumination period is different for each second illumination period and the emission spectrum of the second illumination light is different for each second illumination period as illustrated in FIG. 8. An emission spectrum of the first illumination light may be the same or different for each first illumination period.

Here, it is preferable that the first illumination period is longer than the second illumination period, and it is preferable that the first illumination period is two or more frames. For example, in FIG. 4, in a case where the first emission pattern is set to the first A pattern and the second emission pattern is set to the second A pattern (the number of frames of the second illumination period is the same and the emission spectrum of the second illumination light is the same), the first illumination period is set to two frames and the second illumination period is set to one frame. Since the first illumination light is used to generate the display image to be displayed on the display 17, it is preferable that a bright image is obtained by illuminating the observation target with the first illumination light.

It is preferable that the first illumination light is white light. White includes so-called pseudo white obtained by mixing the violet light V, the blue light B, the green light G, or the red light R as illustrated in FIG. 3, which is substantially equivalent to white in imaging of the subject using the endoscope 12.

The details of the first and second emission patterns, which are switching patterns between the first illumination period and the second illumination period, are determined based on the imaging control of an imaging sensor 43 by an imaging processor 44 and thus, will be described later. The term "frame" refers to a unit of a period including at least a period from a specific timing to the completion of signal readout in the imaging sensor 43.

In this specification, the light quantity ratio includes a case where a ratio of at least one semiconductor light source is 0 (zero). Accordingly, a case where any one or two or more of the semiconductor light sources are not turned on is included. For example, as in a case where the light quantity ratio among the violet light V, the blue light B, the green light G, and the red light R is 1:0:0:0, a case where only one of the semiconductor light sources is turned on and the other three are not turned on is also regarded as having the light quantity ratio.

The light emitted from each of LEDs 20a to 20d (refer to FIG. 2) is incident on a light guide 23 through an optical path coupling unit 22 constituted by a mirror, a lens, and the like. The light guide 23 propagates the light from the optical path coupling unit 22 to the distal end portion 12d of the endoscope 12.

An illumination optical system 30a and an imaging optical system 30b are provided in the distal end portion 12d of the endoscope 12. The illumination optical system 30a has an illumination lens 31, and the observation target is irradiated with the illumination light propagated by the light guide 23 through the illumination lens 31. The imaging optical system 30b includes an objective lens 41 and the imaging sensor 43. Light from the observation target caused by irradiation with the illumination light is incident on the imaging sensor 43 through the objective lens 41 and a zoom lens 42. Accordingly, an image of the observation target is formed on the imaging sensor 43. The zoom lens 42 is a lens for magnifying the observation target and is moved between a telephoto end and a wide end by operating the zoom operation portion 12i.

The imaging sensor 43 is a color sensor of a primary color system and comprises three types of pixels of a blue pixel (B pixel) having a blue color filter, a green pixel (G pixel) having a green color filter, and a red pixel (R pixel) having a red color filter. As illustrated in FIG. 9, a blue color filter BF mainly transmits light in a blue wavelength range, specifically, light in a wavelength range of 380 to 560 nm. A transmittance of the blue color filter BF peaks in the vicinity of a wavelength of 460 to 470 nm. A green color filter GF mainly transmits light in a green wavelength range, specifically, light in a wavelength range of 460 to 620 nm. A red color filter RF mainly transmits light in a red wavelength range, specifically, light in a wavelength range of 580 to 760 nm.

In addition, the imaging sensor 43 is preferably a charge-coupled device (CCD) or a complementary metal oxide semiconductor (CMOS). The imaging processor 44 controls the imaging sensor 43. Specifically, the image signal is output from the imaging sensor 43 by performing signal readout from the imaging sensor 43 by the imaging processor 44. In the first illumination observation mode and the image analysis mode, the imaging processor 44 performs the signal readout in a state where the imaging sensor 43 is exposed to the white light, and thus, a Bc image signal is output from the B pixel of the imaging sensor 43, a Gc image signal is output from the G pixel, and an Rc image signal is output from the R pixel. In the second illumination observation mode and the image analysis mode, the imaging processor 44 performs the signal readout in a state where the imaging sensor 43 is exposed to the special light, and thus, a Bs image signal is output from the B pixel of the imaging sensor 43, a Gs image signal is output from the G pixel, and a Rs image signal is output from the R pixel.

In the image analysis mode, as illustrated in FIG. 10, the imaging processor 44 outputs a first image signal from the imaging sensor 43 by performing the signal readout in a state where the imaging sensor 43 is exposed to the first illumination light in the first illumination period. A period in which the first image signal is output is referred to as a first imaging period. The first image signal includes the Bc image signal output from the B pixel, the Gc image signal output from the G pixel, and the Rc image signal output from the R pixel. Further, the imaging processor 44 outputs a second image signal from the imaging sensor 43 by performing the signal readout in a state where the imaging sensor 43 is exposed to the second illumination light in the second illumination period. A period in which the second image signal is output is referred to as a second imaging period. The second image signal includes the Bs image signal output from the B pixel, the Gs image signal output from the G pixel, and the Rs image signal output from the R pixel.

A correlated double sampling/automatic gain control (CDS/AGC) circuit 45 (refer to FIG. 2) performs correlated double sampling (CDS) or an automatic gain control (AGC) on an analog image signal obtained from the imaging sensor 43. The image signal that has passed through the CDS/AGC circuit 45 is converted into a digital image signal by an analog/digital (A/D) converter 46. The digital image signal after the A/D conversion is input to the processor device 15.

In the processor device 15, a program in a program memory is operated by a central control unit 55 composed of an image control processor, and thus, functions of an image acquisition unit 50, a digital signal processor (DSP) 52, a noise reduction unit 53, the image processing switching unit 54, an examination image acquisition unit 60, an image selection unit 90, and a display control unit 200 are realized.

The image acquisition unit 50 acquires a color image input from the endoscope 12. The color image includes a blue signal (B image signal), a green signal (G image signal), and a red signal (R image signal) output from the B pixel, the G pixel, and the R pixel of the imaging sensor 43. The acquired color image is transmitted to the DSP 52. The DSP 52 performs various types of signal processing, such as defect correction processing, offset processing, gain correction processing, matrix processing, gamma conversion processing, demosaicing processing, and YC conversion processing, on the received color image.

The noise reduction unit 53 performs noise reduction processing by, for example, a moving average method or a median filter method on the color image on which demosaicing processing or the like has been performed in the DSP 52. The noise-reduced color image is input to the image processing switching unit 54.

The image processing switching unit 54 switches a transmission destination of the image signal from the noise reduction unit 53 according to a set mode. Specifically, in a case where the first illumination observation mode is set, the image signal from the noise reduction unit 53 is input to a first illumination light image generation unit 70 of the examination image acquisition unit 60. In a case where the second illumination observation mode is set, the image signal from the noise reduction unit 53 is input to a second illumination light image generation unit 80. In a case where the image analysis mode is set, the image signal from the noise reduction unit 53 is input to the first illumination light image generation unit 70 and the second illumination light image generation unit 80.

Hereinafter, image processing for the first illumination light image, image processing for the second illumination light image, and enhanced image display control processing performed on the image signal transmitted from the noise reduction unit 53 to the examination image acquisition unit 60 through the image processing switching unit 54 will be described.

In a case of the first illumination observation mode, the first illumination light image generation unit 70 performs the image processing for the first illumination light image on the input Rc image signal, Gc image signal, and Bc image signal for one frame. The image processing for the first illumination light image includes color conversion processing such as 3×3 matrix processing, gradation transformation processing, and three-dimensional look up table (LUT) processing, and structure enhancement processing such as color enhancement processing and spatial frequency enhancement. The Rc image signal, Gc image signal, and Bc image signal on which the image processing for the first illumination light image has been performed are transmitted to the display control unit 200 as the first illumination light image.

Figure 11:
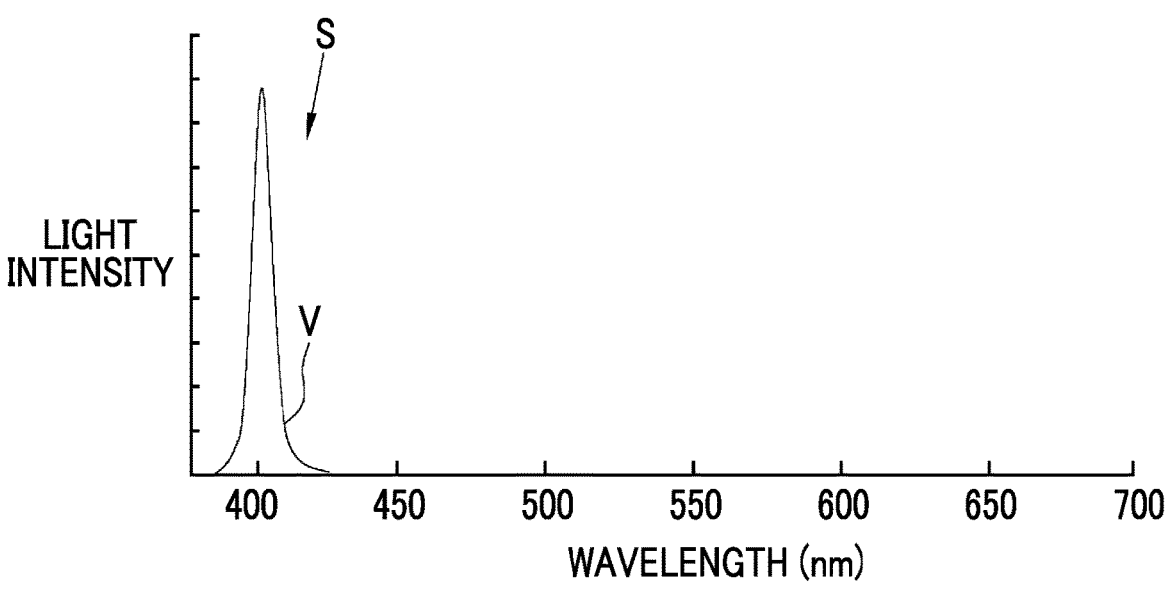
FIG. 11 is a graph illustrating a spectrum of second illumination light.

In a case of the second illumination observation mode, the second illumination light image generation unit 80 performs the image processing for the second illumination light image on the input Rs image signal, Gs image signal, and Bs image signal for one frame. The image processing for the second illumination light image is processing performed on the Bs image signal, the Gs image signal, and the Rs image signal obtained by emitting the second illumination light with a second illumination light emission spectrum S. It is preferable that the second illumination light emitted with the second illumination light emission spectrum S is light emitting violet light V (a peak wavelength is, for example, 410 nm±10) as illustrated in FIG. 11.

The image processing for the second illumination light image is processing of assigning the Bs image signals to a B channel, G channel, and R channel for display and adjusting a tone and a gradation balance. The image processing for the second illumination light image includes color conversion processing such as 3×3 matrix processing, gradation transformation processing, and three-dimensional look up table (LUT) processing, and structure enhancement processing such as color enhancement processing and spatial frequency enhancement. The second illumination light image in which a blood vessel or a structure at a specific depth is enhanced is obtained by the image processing for the second illumination light image. The Rs image signal, Gs image signal, and Bs image signal on which the image processing for the second illumination light image has been performed are transmitted to the display control unit 200 as the second illumination light image. The display control unit 200 displays the second illumination light image on the display 17.

In a case of the image analysis mode, the first illumination light image generation unit 70 performs the image processing for the first illumination light image on the Rc image signal, Gc image signal, and Bc image signal for one frame to obtain the first illumination light image. Further, the second illumination light image generation unit 80 performs the image processing for the second illumination light image on the input Rs image signal, Gs image signal, and Bs image signal for one frame to obtain the second illumination light image. In this specification, claims, drawings, and abstract, the term "examination image" simply refers to the first illumination light image and/or the second illumination light image.

In a case of the image analysis mode, generally, the first illumination light image is transmitted to the display control unit 200 as the display image and is displayed on the display 17. The second illumination light image is used for calculating a lesion evaluation value to be described later. The second illumination light image can be set to be transmitted to the display control unit 200 and displayed on the display 17.

Hereinafter, the image analysis mode will be described. In the image analysis mode, the examination image is divided into a plurality of regions, and then the lesion is analyzed. In the image analysis mode of the present embodiment, there are two methods for finally outputting a lesion evaluation value for a lesion. One is a method of transmitting an examination image to an image division unit 100 to divide the image, evaluating a quality of the examination image with respect to a divided region, and then evaluating a lesion in the divided region. The other is a method of inputting an examination image to a third classifier 130, outputting the image in which a portion not suitable for lesion evaluation is deleted in advance, dividing the image, and evaluating the lesion in a divided region.

In a case of the image analysis mode, the examination image generated by the examination image acquisition unit 60 is transmitted to the image selection unit 90. The image selection unit 90 selects an input image to be input to the image division unit 100 or the third classifier 130 from the examination images.

In a case of the image analysis mode, as illustrated in FIG. 10, the first illumination light image is obtained by outputting the first image signal in the first illumination period, and the second illumination light image is obtained by outputting the second image signal in the second illumination period. The image selection unit 90 selects the first illumination light image and/or the second illumination light image as the input image. A user can arbitrarily set which of the first illumination light image and/or the second illumination light image is used as the input image. The input image selected by the image selection unit 90 is transmitted to an image input unit 92 of the computer 16.

It is preferable to select the second illumination light image as the input image. This is because the second illumination light image is an image in which a blood vessel is enhanced and is thus an image in which a lesion is more easily recognized than the first illumination light image, and thus an accuracy of a lesion evaluation value to be finally obtained can be improved.

Figure 12:
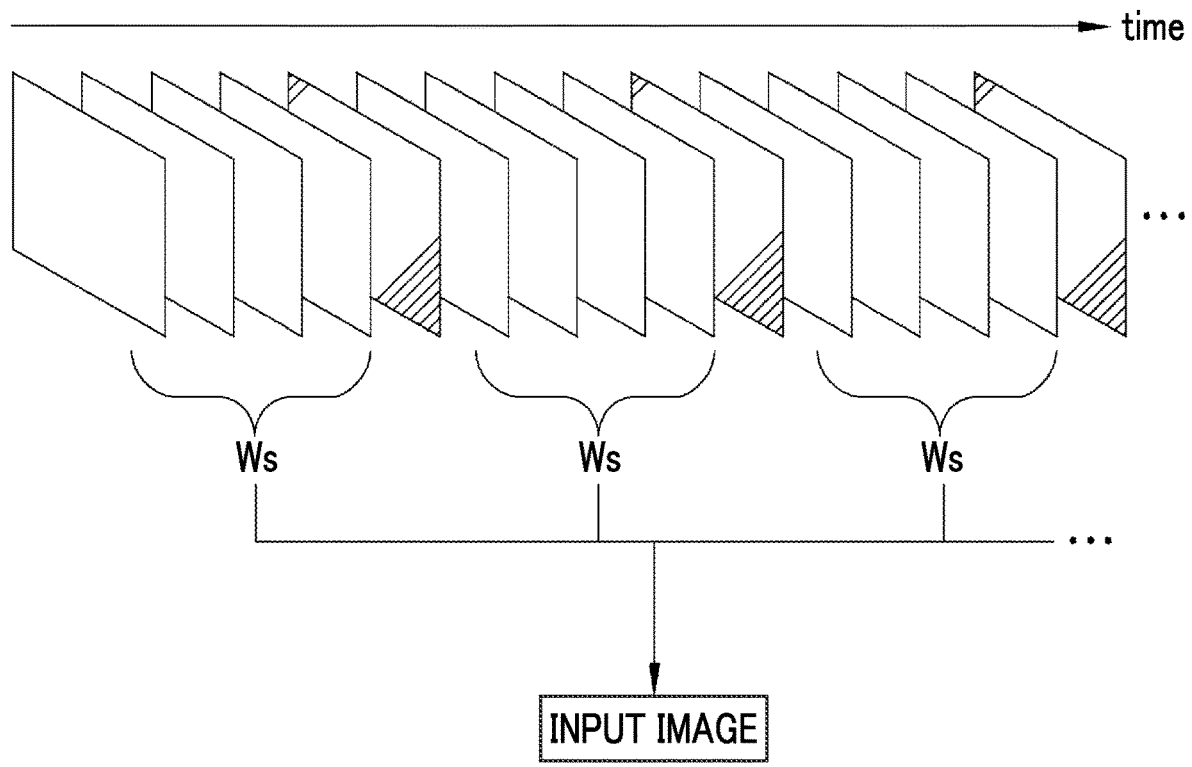
FIG. 12 is an explanatory diagram illustrating functions of an image selection unit in a case where a first illumination light image is an input image.

In a case where the first illumination light image is selected as the input image, for example, as illustrated in FIG. 12, the first illumination light image Ws among the examination images obtained in the image analysis mode is selected as the input image by the image selection unit 90. The selected input image is input to the image division unit 100 or the third classifier 130. In a specific example illustrated in FIG. 12, the first illumination light images of all frames obtained in the first illumination period are selected as the input image, but the frame selected as the input image in the first illumination period may be selected. For example, the first illumination light image may be selected as the input image for every other frame in the first illumination period, or the first illumination light image of the frame immediately before entering the second illumination period may be selected as the input image.

Figures 13, 14:
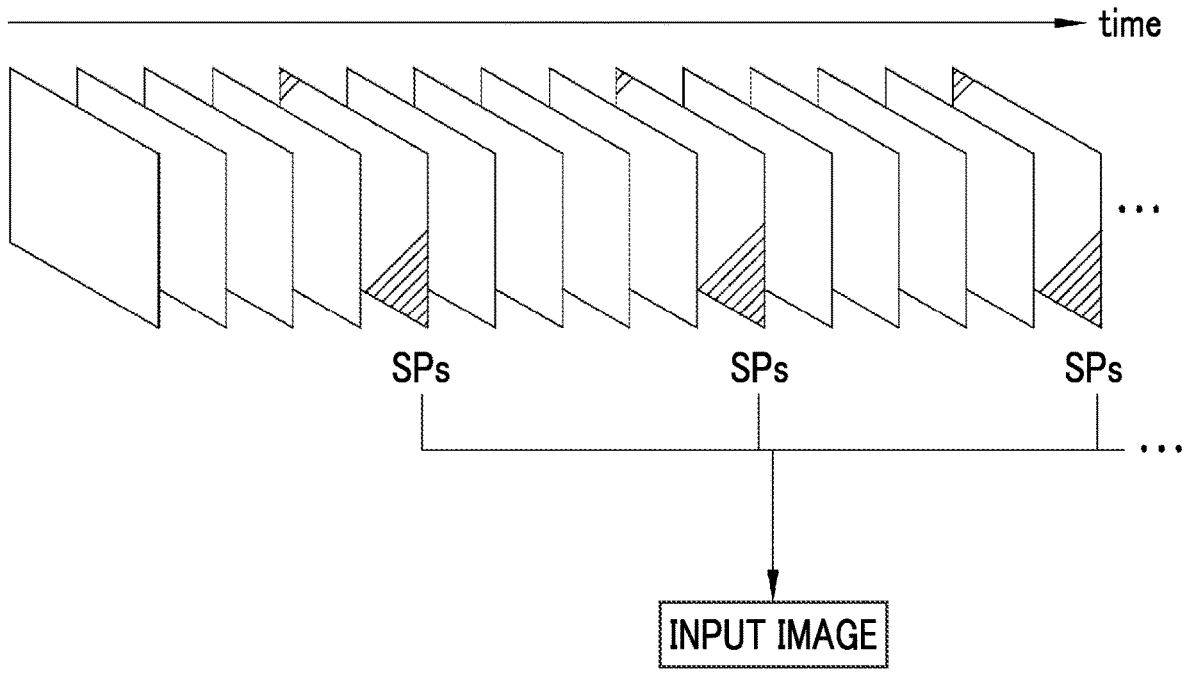
FIG. 13 is an explanatory diagram illustrating functions of the image selection unit in a case where a second illumination light image is the input image.
FIG. 14 is an image diagram illustrating an example in which an image division unit divides the input image.

In a case where the second illumination light image is selected as the input image, for example, as illustrated in FIG. 13, the second illumination light image SPs among the examination images obtained in the image analysis mode is selected as the input image by the image selection unit 90. The selected input image is input to the image division unit 100 or the third classifier 130. In a specific example illustrated in FIG. 13, the second illumination light images of all frames obtained in the second illumination period are selected as the input image, but the frame to be selected as the input image in the second illumination period may be selected. For example, the second illumination light image may be selected as the input image in the second illumination period every other time or once every plurality of times.

The computer 16 includes the image input unit 92, the image division unit 100, a first classifier 110, a second classifier 120, the third classifier 130, an image evaluation value calculation unit 140, a site evaluation value calculation unit 150, and an overall evaluation value calculation unit 160 (refer to FIG. 2). In the computer 16, a program in a program memory is operated by a control unit (not illustrated) composed of an image control processor, and thus, functions of the image input unit 92, the image division unit 100, the first classifier 110, the second classifier 120, the third classifier 130, the image evaluation value calculation unit 140, the site evaluation value calculation unit 150, and the overall evaluation value calculation unit 160 are realized. The computer 16 and/or the light source processor 21 may be included in the processor device 15.

The first classifier 110, the second classifier 120, and the third classifier 130 are classifiers generated using machine learning and/or image processing. Deep learning is preferably used for machine learning, and for example, a multi-layer convolutional neural network is preferably used. The machine learning includes decision tree, support vector machine, random forest, regression analysis, supervised learning, semi-supervised learning, unsupervised learning, reinforcement learning, deep reinforcement learning, learning using a neural network, a generative adversarial network, and the like in addition to deep learning.

A case where the input image is transmitted to the image division unit 100 will be described. The image division unit 100 divides the input image into a plurality of regions. For example, the input image is divided into a plurality of lattice-like regions as illustrated in FIG. 14. In a specific example of FIG. 14, the input image is divided into a plurality of regions, that is, 16 regions from a region A to a region P. A shape of division is not limited to a lattice form, and may be any shape capable of subdividing the input image, for example, a polygonal shape such as a hexagon or a shape made up of curves. In addition, the plurality of regions may be cut out in random shapes having different shapes and sizes depending on locations.

Figure 15:
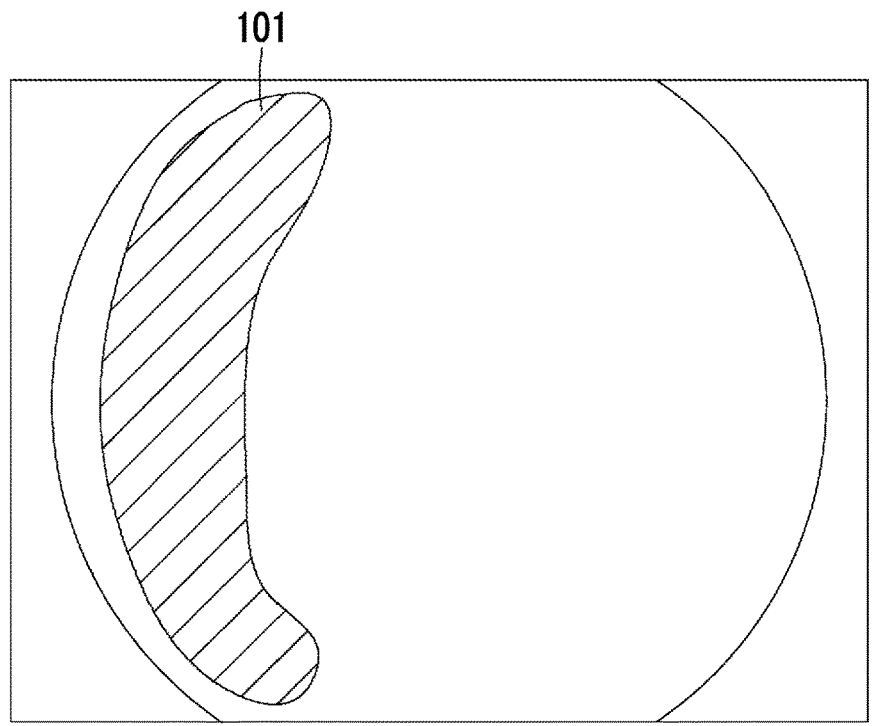
FIG. 15 is an image diagram illustrating an example in which a liquid pool is included in an examination image.
Figure 16:
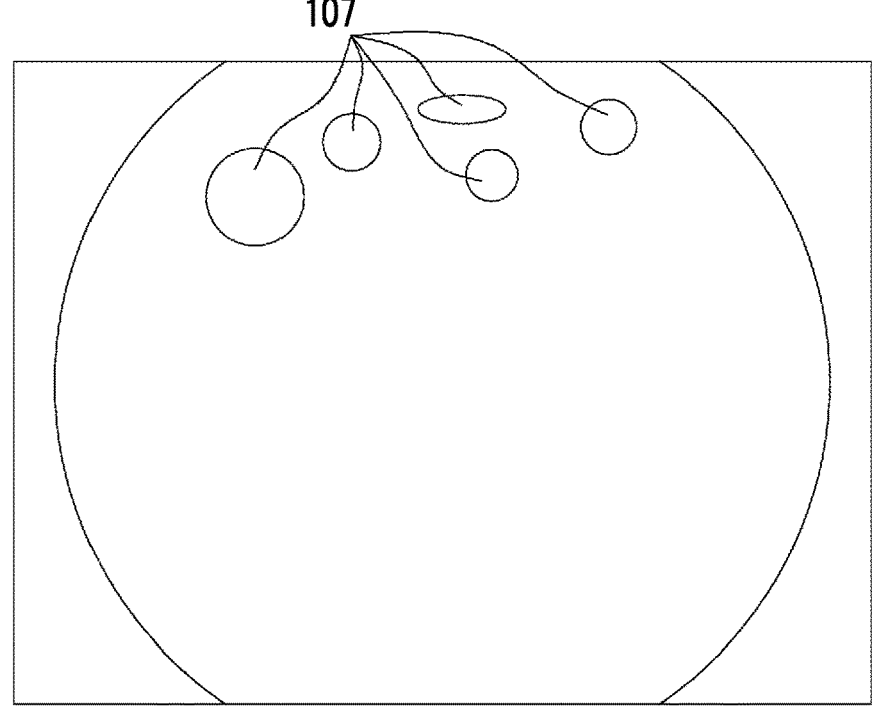
FIG. 16 is an image diagram illustrating an example in which bubbles are included in the examination image.
Figure 17:
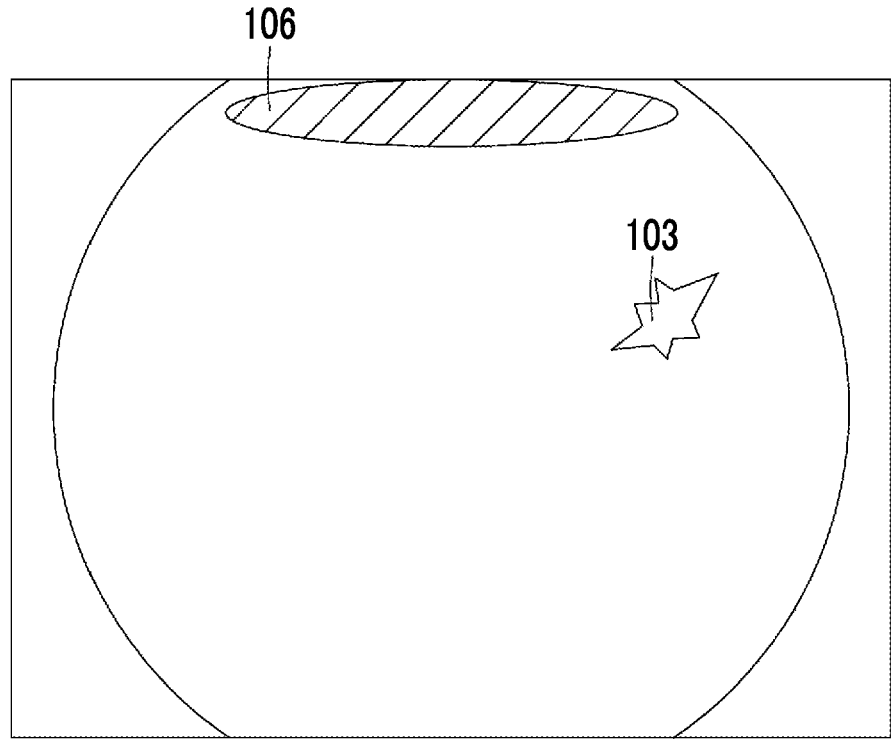
FIG. 17 is an image diagram illustrating an example in which a reflection is included in the examination image.
Figure 18A:
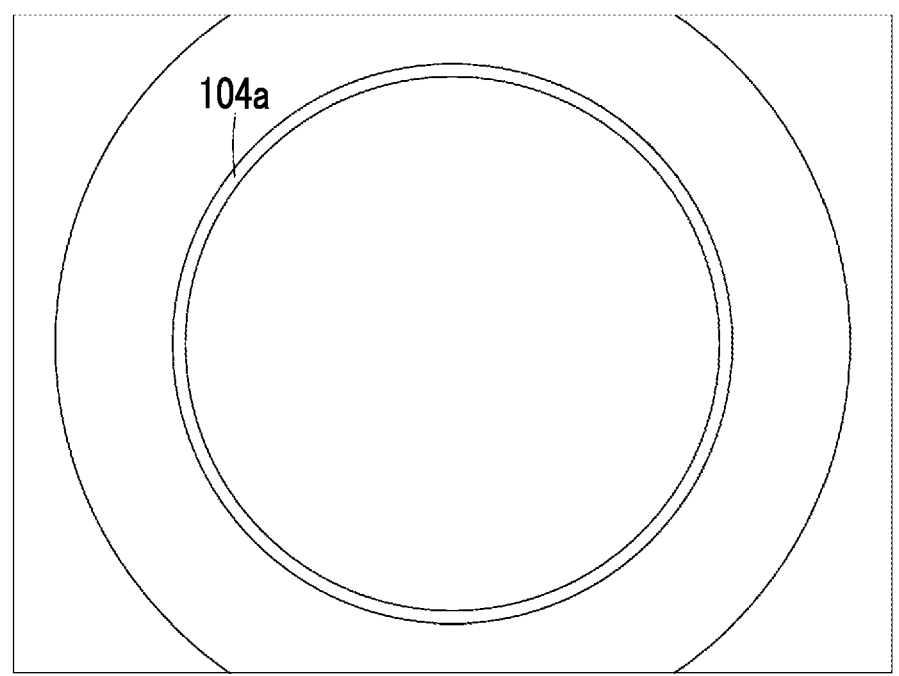
FIG. 18A is an image diagram illustrating an example in which an edge portion of a cap is included in the examination image.
Figure 18B:
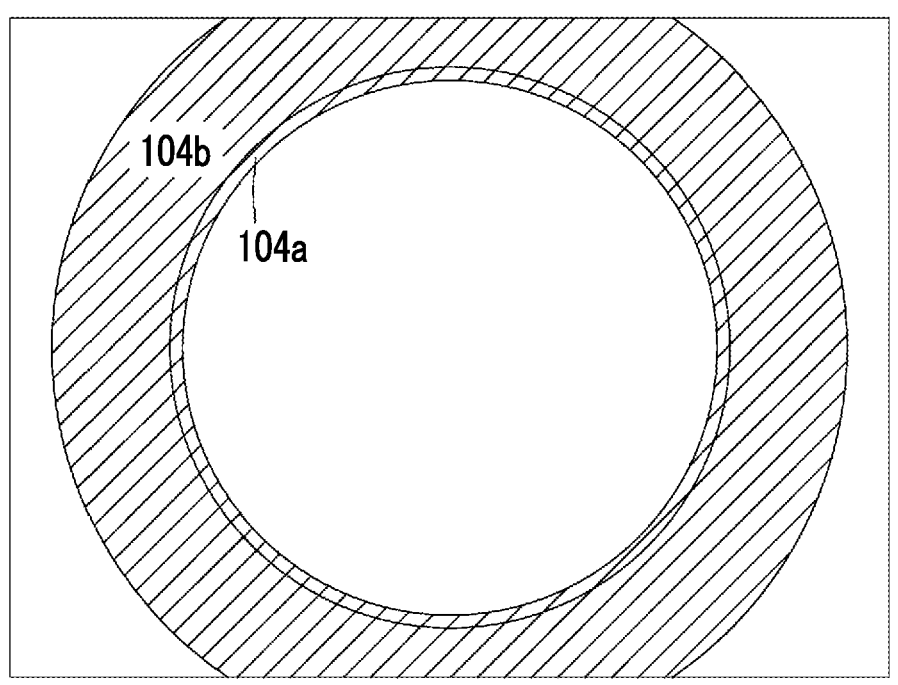
FIG. 18B is an image diagram illustrating an example in which an entire cap region including the edge portion of the cap is set as an evaluation inhibition target.

The image division unit 100 preferably divides the input image into a region of interest that may be a lesion or an evaluation inhibition target other than the region of interest in a size that can be determined. The evaluation inhibition target refers to a structure or an artifact that is not suitable for output of a lesion evaluation value, which is a value for evaluating a region of interest of the input image, and that causes a decrease in accuracy of the evaluation. For example, a specific pool portion 101 such as a puddle, a blood pool, or a liquid pool of an excessive chemical liquid that covers an observation target as illustrated in FIG. 15, or bubbles 107 as illustrated in FIG. 16 are included. In addition, as illustrated in FIG. 17, a distortion (distortion due to an objective lens used for imaging an observation target) and blurriness of an image peripheral portion generated in an image peripheral portion 106, and a reflection 103 such as halation are included. Further, in a case where a cap (hood) is mounted to the distal end portion 12d of the endoscope 12 and an edge portion 104a of the cap appears on the input image, the evaluation inhibition target includes the edge portion 104a of the cap as illustrated in FIG. 18A or an entire cap region 104b including the edge portion 104a of the cap as illustrated in FIG. 18B.

Figure 19:
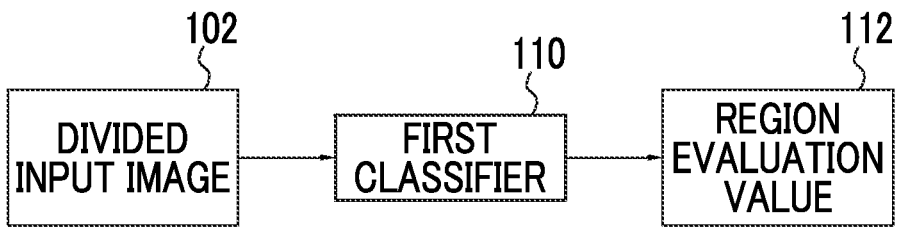
FIG. 19 is a block diagram illustrating functions of a first classifier.

As illustrated in FIG. 19, the input image 102 divided into a plurality of regions by the image division unit 100 is input to the first classifier 110. The first classifier 110 outputs a region evaluation value 112 for each of a plurality of regions included in the input image. The region evaluation value 112 is an evaluation value for the quality of the divided input image 102 itself. That is, the region evaluation value 112 is a value obtained by digitizing whether or not an evaluation inhibition target is included in the divided input image 102 and in a case where the evaluation inhibition target is included, how much the evaluation inhibition target affects the output of the lesion evaluation value, in order to improve an accuracy of the output of the lesion evaluation value to be described later.

Figure 20:
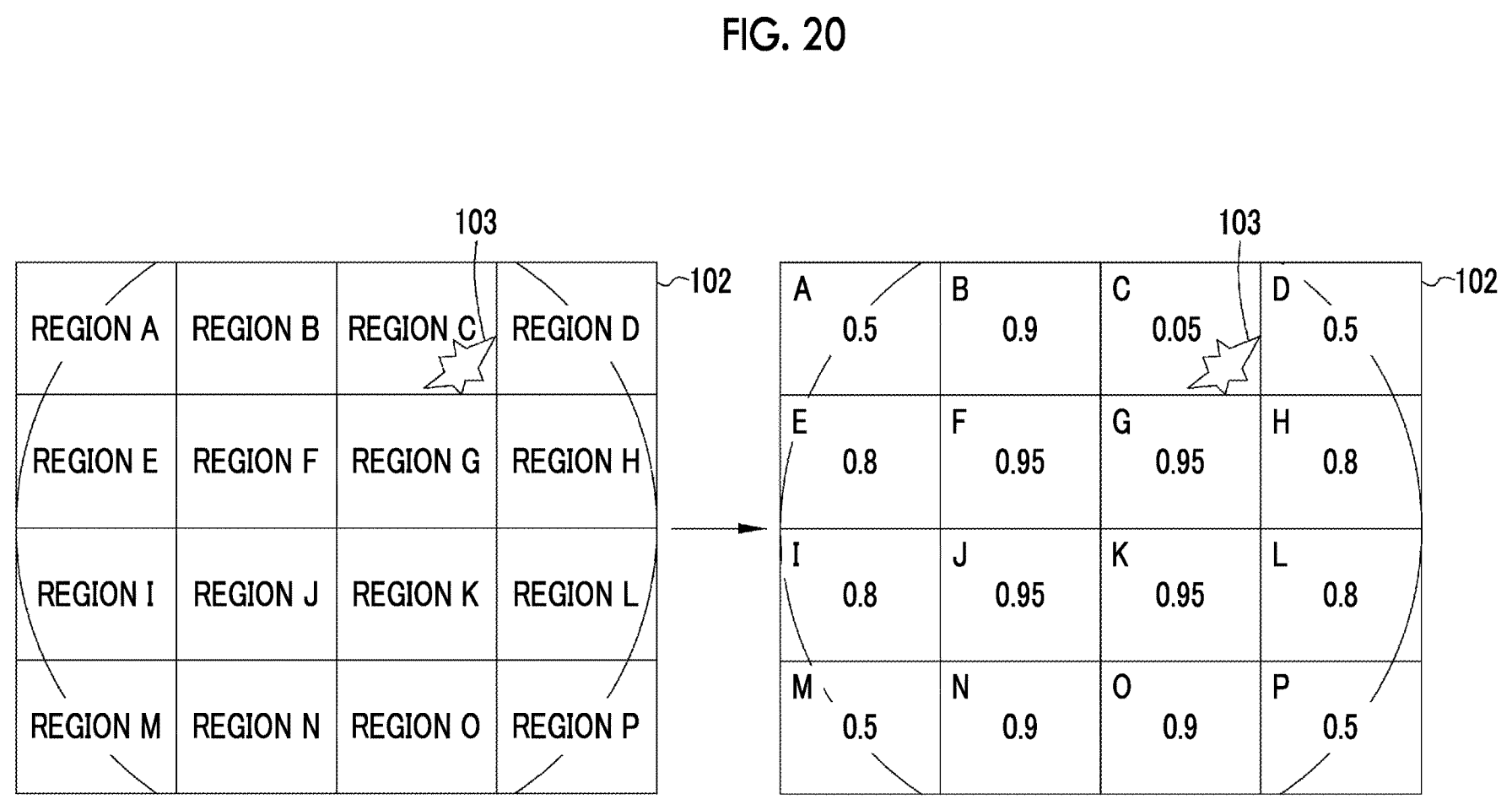

In an example illustrated in FIG. 20, the region evaluation value of 0.5 is output for a region A of the divided input image 102. Similarly, for the other regions, a region evaluation value of 0.9 is output for a region B, a region evaluation value of 0.05 is output for a region C, a region evaluation value of 0.5 is output for a region D, a region evaluation value of 0.8 is output for a region E, a region evaluation value of 0.95 is output for a region F, a region evaluation value of 0.95 is output for a region G, a region evaluation value of 0.8 is output for a region H, a region evaluation value of 0.8 is output for a region I, a region evaluation value of 0.95 is output for a region J, a region evaluation value of 0.95 is output for a region K, a region evaluation value of 0.8 is output for a region L, a region evaluation value of 0.5 is output for a region M, a region evaluation value of 0.9 is output for a region N, a region evaluation value of 0.9 is output for a region O, and a region evaluation value of 0.5 is output for a region P.

In a case where the evaluation inhibition target is not included in the region and the determination of the region of interest can be appropriately performed, the first classifier 110 calculates the region evaluation value to be high. On the other hand, in a case where the evaluation inhibition target is included in the region, the first classifier 110 calculates the region evaluation value to be low. That is, the region evaluation value is a value that varies depending on what kind of and to what extent the evaluation inhibition target is included in the input image 102.

In the specific example of FIG. 20, the region B (region evaluation value 0.9), the region E (region evaluation value 0.8), the region F (region evaluation value 0.95), the region G (region evaluation value 0.95), the region H (region evaluation value 0.8), the region I (region evaluation value 0.8), the region J (region evaluation value 0.95), the region K (region evaluation value 0.95), the region L (region evaluation value 0.8), the region N (region evaluation value 0.9), and the region O (region evaluation value 0.9) are normal mucous membranes and are regions in which the determination of the region of interest can be appropriately performed. On the other hand, the region C (region evaluation value 0.05) has a reflection 103. Since the region A, the region D, the region M, and the region P are ends of a visual field of the endoscope, distortion occurs. Therefore, lower region evaluation values are output for the region A, the region C, the region D, the region M, and the region P including the evaluation inhibition target than those for the region B, the region E, the region F, the region G, the region H, the region I, the region J, the region K, the region L, the region N, and the region O not including the evaluation inhibition target.

Figure 21:
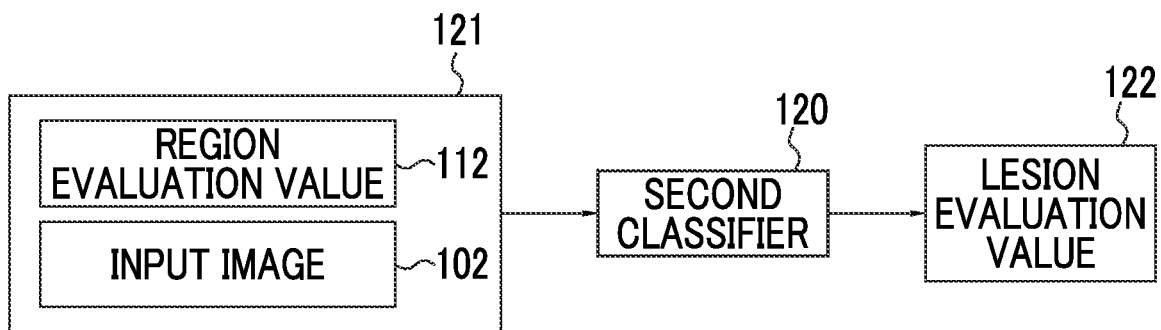
FIG. 21 is a block diagram illustrating functions of a second classifier in a case where an input image in which the region evaluation value is added to the divided region is input to the second classifier.

As illustrated in FIG. 21, an input image 121 in which the region evaluation values are added to a plurality of regions is input to the second classifier 120. The second classifier 120 outputs a lesion evaluation value 122 for the input image. The second classifier 120 may output the lesion evaluation value for each region of the divided input image, or may output the lesion evaluation value for the entire input image.

The lesion evaluation value is an evaluation value indicating a degree of the lesion in the input image. It is preferable that the second classifier 120 is trained with an examination image to which a diagnosis result by a specialist regarding an image diagnosis of an endoscope is given. Furthermore, it is preferable that the second classifier 120 is trained with an examination image to which a diagnosis of an endoscopic image and a diagnosis result obtained by performing a pathological examination (biopsy) are given.

It is preferable that the lesion evaluation value is an evaluation value based on a known scoring method. It is preferable that the lesion evaluation value is output based on an evaluation index for ulcerative colitis. For example, a score based on an ulcerative colitis endoscopic index of severity (UCEIS) may be used.

The UCEIS is characterized in that, regarding an evaluation of activity of ulcerative colitis in the endoscopic image, as in Table 1 (Yasuo Suzuki, Fumihito Hirai, et al., Disease Activity Evaluation Index Collection for Inflammatory Bowel disease, 2nd edition, "Research on Intractable Inflammatory Bowel Disorders (Suzuki group)" by Policy Research Project for Intractable Diseases supported by Health and Labor Sciences Research Grant, March 2020; 16 is modified), each of a visible vascular pattern, bleeding, an erosion, and an ulcer is individually evaluated at a site with the strongest findings, and the evaluation results are summed up to obtain a total score. For example, a case where a total score of UCEIS is 2 to 4 is evaluated as mild, a case where the total score is 5 to 6 is evaluated as moderate, and a case where the total score is 7 to 8 is evaluated as severe.

TABLE 1

| Evaluation item | Scale | Definition | Score |
|---|---|---|---|
| Visible vascular pattern | Normal | A normal visible vascular pattern. A dendritic blood vessel is clearly observed, but a peripheral area of the dendritic blood vessel is blurred or partially disappears. | 0 |
| | Partial disappearance | A visible vascular pattern partially disappears. | 1 |
| | Disappearance | A visible vascular pattern completely disappears. | 2 |
| Bleeding | None | No bleeding | 0 |
| | Mucosal bleeding | Several punctate or linear suspected blood clots are seen on a mucosal surface upon insertion of an endoscope but can be removed with irrigation. | 1 |
| | Mild luminal bleeding | A small amount of bleeding is seen in a lumen. | 2 |
| | Moderate or severe luminal bleeding | Obvious bleeding is seen upon insertion of an endoscope. Or, even after irrigation, oozing bleeding is seen from a mucous membrane. Or, oozing bleeding is seen from a hemorrhagic mucous membrane. | 3 |
| Erosion and ulcer | None | A normal mucous membrane where an erosion and an ulcer are not seen. | 0 |
| | Erosion | A small mucosal defect of 5 mm or less with a flat white or yellowish peripheral edge. | 1 |
| | Shallow ulcer | A distinct ulcer covered with white furriness compared with an erosion, which is a | 2 |

TABLE 1-continued

| Evaluation item | Scale | Definition | Score |
|---|---|---|---|
| | | mucosal defect exceeding 5 mm but remains superficial. | |
| | Deep ulcer | A deep ulcer with a slightly raised peripheral edge. | 3 |

Other evaluation indices for ulcerative colitis, for example, Severity Classification of Research Group regarding Intractable Inflammatory Bowel Disorders, Truelove-Witts index, Powell-Tuck index, Seo index, Lichtiger index, Sutherland index (disease activity index), Mayo score, Rachmilewitz index, Pouchitis disease activity index (PDAI), Baron index, modified Baron index, Matts classification, Simple clinical colitis activity index (SCCAI), Pediatric ulcerative colitis activity index (PUCAI), Geboes histopathology score (GHS) and the like, may be used as the lesion evaluation value.

The lesion evaluation value may be output based on a feature amount. It is preferable that the feature amount is classified by a position of the observation target in at least any one of a surface layer, an intermediate layer, or a deep layer. Additionally, it is preferable that the feature amount is a shape or color of the observation target, or a value obtained from the shape, color, or the like. Examples of items of the feature amount include a blood vessel density, a blood vessel shape, the number of branches of a blood vessel, a thickness of a blood vessel, a length of a blood vessel, a meandering degree of a blood vessel, an invasion depth of a blood vessel, a gland duct shape, a gland duct opening shape, a length of a gland duct, a meandering degree of a gland duct, color information, and luminance. The feature amount is preferably at least any one of these or a value obtained by combining two or more of these. The items of the feature amount are not limited to thereto and may be appropriately added in accordance with a use situation.

The lesion evaluation value may be output based on the presence or absence of the region of interest and a degree thereof. The region of interest is, for example, a region including an inflammatory portion (including a portion with a change such as bleeding or atrophy in addition to a so-called inflammation), a benign tumor, a malignant tumor, a colonic diverticulum, a treatment scar (an endoscopic mucosal resection (EMR) scar, an endoscopic submucosal dissection (ESD) scar, or a clip portion), a bleeding point, a perforation, a vascular abnormality, a cauterization scar due to heating or a marking portion marked by coloring with a coloring agent, a fluorescent agent, or the like, or a biopsy performed portion where a biopsy is performed. That is, a region including a lesion, a region having a possibility of a lesion, a region subjected to a certain treatment such as a biopsy, a treatment tool such as a clip or forceps, a region that needs to be observed in detail regardless of the possibility of a lesion, such as a dark region (a region where observation light is difficult to reach due to the back of a fold (pleat) or depth of a lumen), or the like can be the region of interest.

Figure 22:
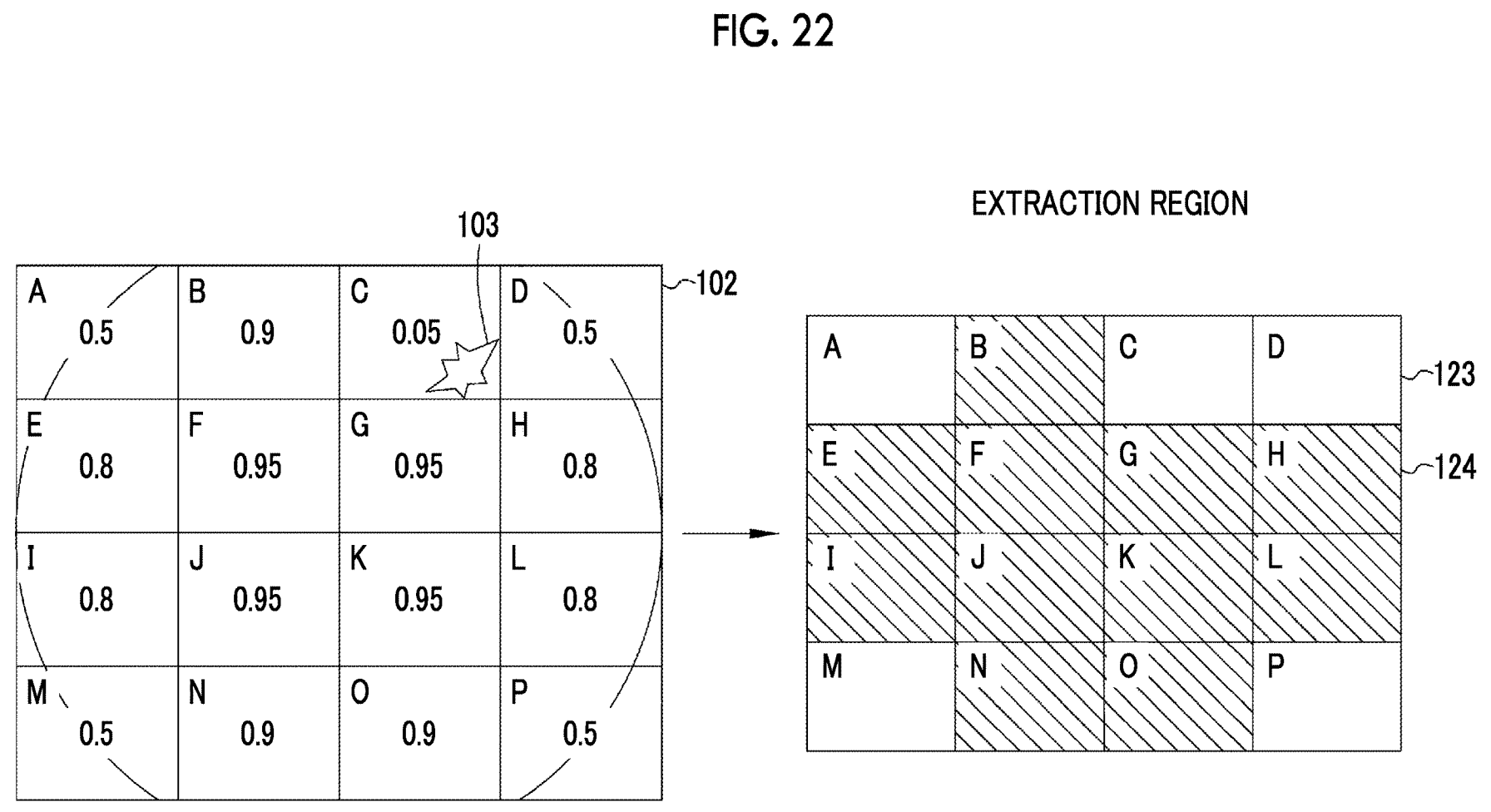

It is preferable that the input image to be input to the second classifier 120 is an input image including an extraction region extracted based on the region evaluation value added to the region divided by the image division unit 100. In this case, an extraction region 124 (a hatched region in FIG. 22) as illustrated in FIG. 22 among a plurality of divided regions is input to the second classifier 120. In FIG. 22, a non-selected region 123 is indicated by a white region.

In a case where the region evaluation value is added to each of the divided regions of the input image, the image to be input to the second classifier 120 may be extracted based on the region evaluation value. For example, in a case where there is a region to which a region evaluation value lower than that of an adjacent region by a certain numerical value or more is output, the region may not be extracted. According to the above-described configuration, the accuracy of the evaluation of the lesion on the image can be improved by performing the evaluation of the lesion after removing the region which is not suitable for the evaluation of the lesion on the examination image in advance.

Further, a threshold value may be provided as a criterion for extracting the extraction region, and a region of equal to or larger than the threshold value may be input to the second classifier 120 as the extraction region. For example, in a case where the threshold value of the extraction region is set to 0.6, in the specific example of FIG. 22, the extraction region 124 is a hatched region, and the region 123 not selected as the extraction region 124 is a white region. The region of less than the threshold value is a region including an evaluation inhibition target such as a puddle, a blood pool, a liquid pool, a bubble, a distortion, blurriness, a reflection, or a cap.

The second classifier 120 may output the lesion evaluation value for the region to which the region evaluation value is added, without extracting the region. Using a specific example of output of the lesion evaluation value in FIG. 23 (see also FIG. 20), the region B (region evaluation value 0.9), the region E (region evaluation value 0.8), the region F (region evaluation value 0.95), the region G (region evaluation value 0.95), the region H (region evaluation value 0.8), the region I (region evaluation value 0.8), the region J (region evaluation value 0.95), the region K (region evaluation value 0.95), the region L (region evaluation value 0.8), the region N (region evaluation value 0.9), and the region O (region evaluation value 0.9) are normal mucous membranes and are regions in which the determination of the region of interest can be appropriately performed. On the other hand, the region C (region evaluation value 0.05) has a reflection 103. Since the region A, the region D, the region M, and the region P are ends of a visual field of the endoscope, distortion occurs.

Figure 23:
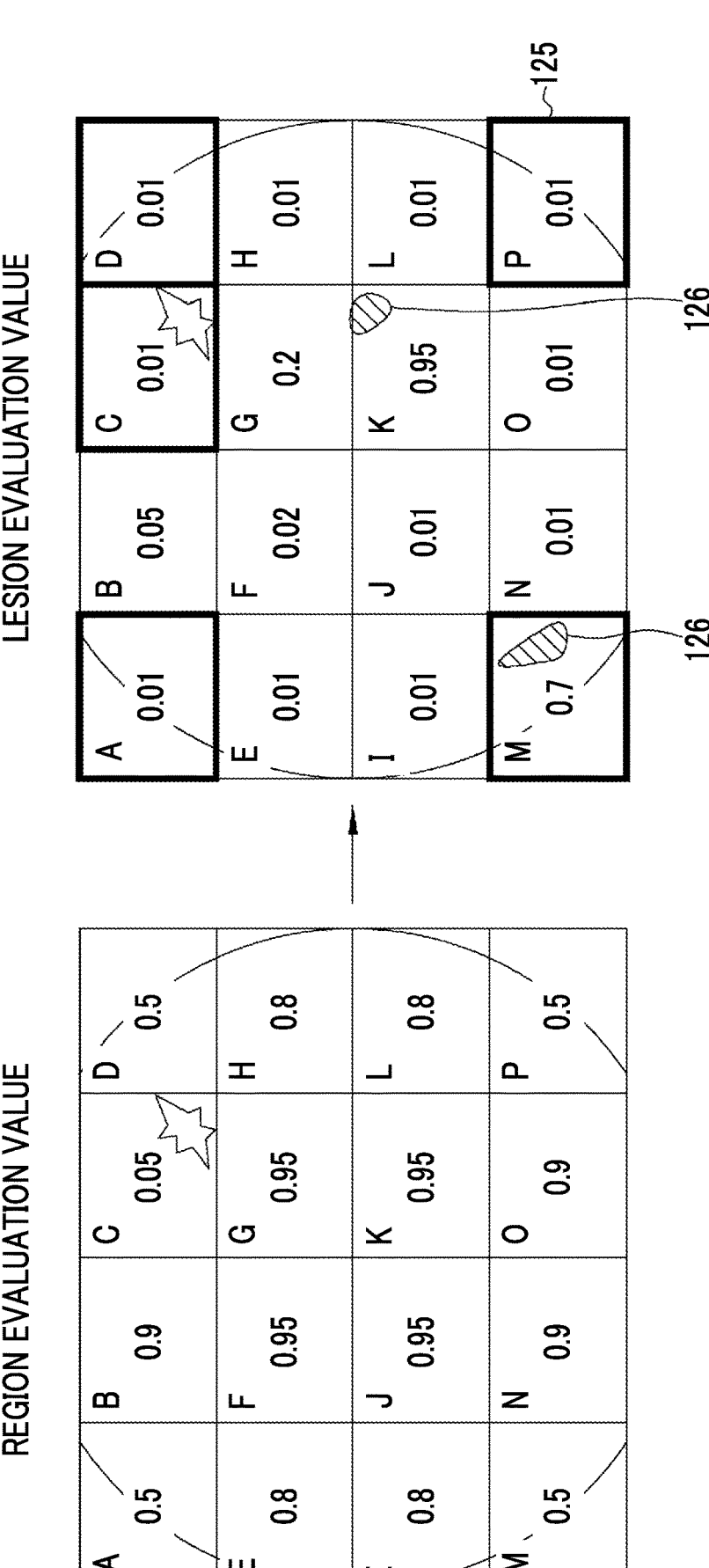
FIG. 23 is an explanatory diagram illustrating an example of calculation of a lesion evaluation value.

In the specific example of the output of the lesion evaluation value in FIG. 23, a lesion evaluation value of 0.01 is output for the region A. Similarly, for the other regions, a lesion evaluation value of 0.05 is output for the region B, a lesion evaluation value of 0.01 is output for the region C, a lesion evaluation value of 0.01 is output for the region D, a lesion evaluation value of 0.01 is output for the region E, a lesion evaluation value of 0.02 is output for the region F, a lesion evaluation value of 0.2 is output for the region G a lesion evaluation value of 0.01 is output for the region H, a lesion evaluation value of 0.01 is output for the region I, a lesion evaluation value of 0.01 is output for the region J, a lesion evaluation value of 0.95 is output for the region K, a lesion evaluation value of 0.01 is output for the region L, a lesion evaluation value of 0.7 is output for the region M, a lesion evaluation value of 0.01 is output for the region N, a lesion evaluation value of 0.01 is output for the region O, and a lesion evaluation value of 0.01 is output for the region P. The lesion evaluation values of the regions K and M including a region of interest 126 are output to be higher than those for the other regions.

In this case, high-accuracy lesion evaluation values can be output for the region B (region evaluation value 0.9, lesion evaluation value 0.05), the region E (region evaluation value 0.8, lesion evaluation value 0.01), the region F (region evaluation value 0.95, lesion evaluation value 0.02), the region G (region evaluation value 0.95, lesion evaluation value 0.2), the region H (region evaluation value 0.8, lesion evaluation value 0.01), the region I (region evaluation value 0.8, lesion evaluation value 0.01), the region J (region evaluation value 0.95, lesion evaluation value 0.01), the region K (region evaluation value 0.95, lesion evaluation value 0.95), the region L (region evaluation value 0.8, lesion evaluation value 0.01), the region N (region evaluation value 0.9, lesion evaluation value 0.01), and the region O (region evaluation value 0.9, lesion evaluation value 0.01), which do not include the evaluation inhibition target.

On the other hand, since the portion of the reflection 103 of the region C (region evaluation value 0.05, the lesion evaluation value 0.01) has high luminance and the image is hardly seen, the output accuracy of the lesion evaluation value is greatly reduced. For the region A (region evaluation value 0.5, lesion evaluation value 0.01), the region D (region evaluation value 0.5, lesion evaluation value 0.01), the region M (region evaluation value 0.5, lesion evaluation value 0.7), and the region P (region evaluation value 0.5, lesion evaluation value 0.01), since the distortion is generated, the output accuracy of the lesion evaluation value is slightly lowered, but the presence or absence of the lesion can be determined to some extent like the region M (region evaluation value 0.5, lesion evaluation value 0.7). In a case where the lesion evaluation value is output without extracting a region, a region having a low region evaluation value such as the region C, the region A, the region D, the region M, and the region P may be displayed by being marked with a frame 125, a color, or the like as illustrated in FIG. 23. With the above configuration, it is possible to visualize a certain quality of an image with the certain quality and to evaluate a lesion while ensuring a certain quality.

Figure 24:
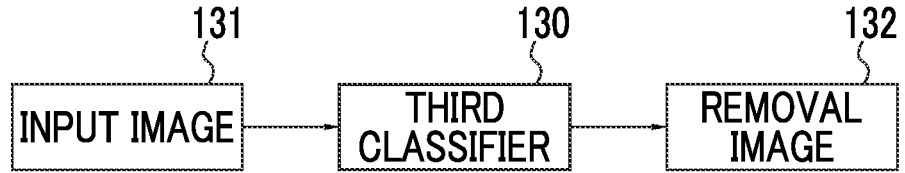
FIG. 24 is an explanatory diagram illustrating functions of a third classifier.
Figure 25:
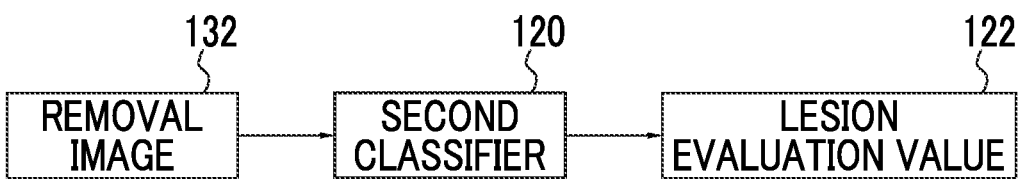
FIG. 25 is an explanatory diagram illustrating functions of the second classifier in a case where a removal image is input.

The image input to the second classifier 120 may be an image in which the evaluation inhibition target has been removed using machine learning in advance. As illustrated in FIG. 24, in a case where the input image 131 is input to the third classifier 130, a removal image 132 in which the evaluation inhibition target is removed is output. The removal image 132 is transmitted to the image division unit 100 and is divided into a plurality of regions. As illustrated in FIG. 25, the removal image 132 divided into the plurality of regions is input to the second classifier 120. The second classifier 120 outputs the lesion evaluation value 122 for the removal image 132. The second classifier 120 may output the lesion evaluation value for each region of the removal image 132 divided into the plurality of regions, or may output the lesion evaluation value for the entire removal image 132 of one frame. With the above configuration, it is possible to evaluate the lesion after removing a portion not suitable for evaluating the lesion in advance, regardless of the image division method, and to improve a reliability degree of the evaluation for the lesion.

Figure 26:
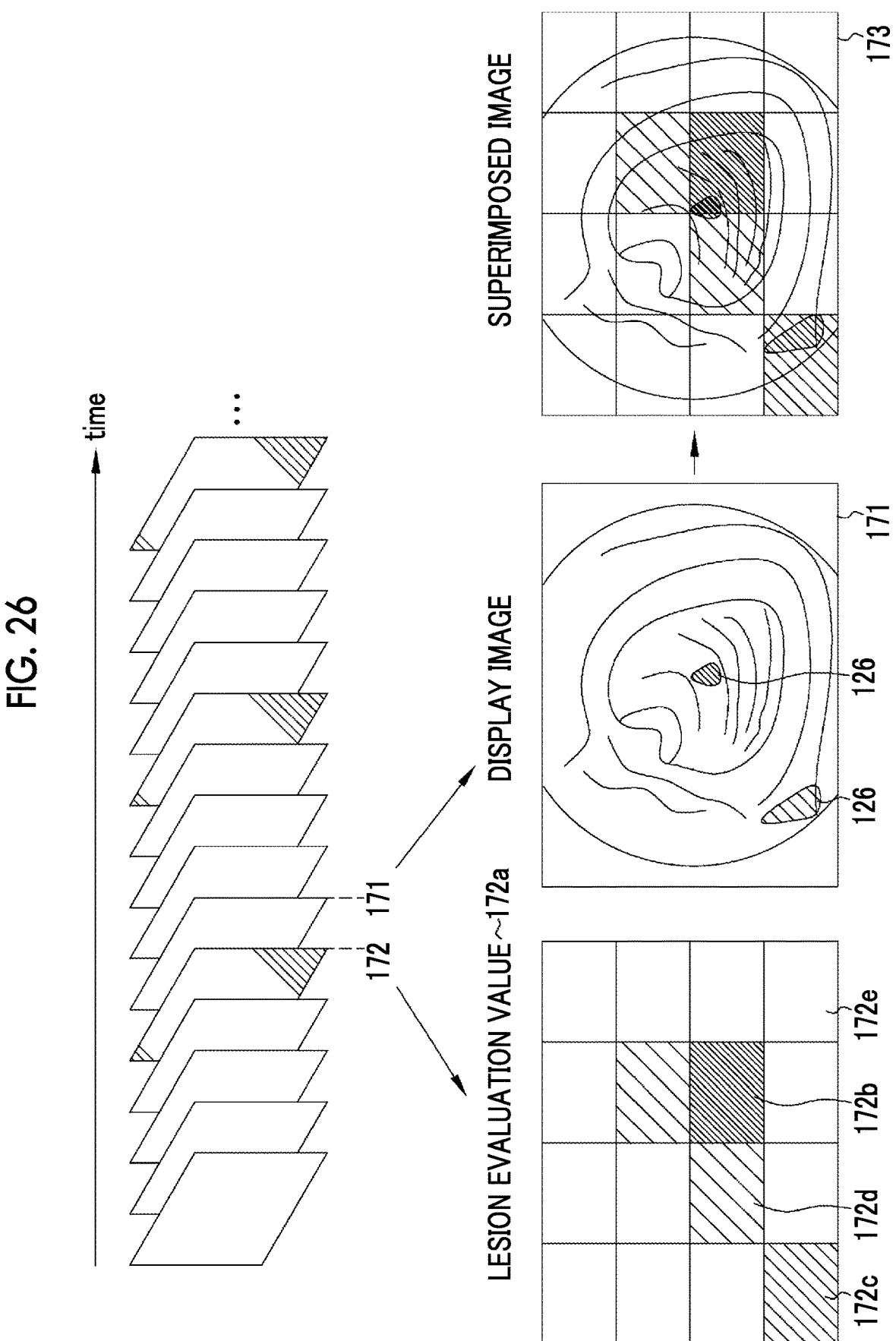
FIG. 26 is an explanatory diagram illustrating an example in which a superimposed image is generated by superimposing the lesion evaluation value output from the examination image of a frame immediately before a display image.

It is preferable that the lesion evaluation value is displayed together with the display image. It is preferable that the display image and the lesion evaluation value are transmitted to the display control unit 200 and as illustrated in FIG. 26, a lesion evaluation value 172a output from an examination image 172 of a frame immediately before a display image 171 is superimposed on the display image 171 to generate and display a superimposed image 173. The lesion evaluation value shown in the superimposed image may be displayed as a numerical value. In addition, as in the superimposed image 173 illustrated in FIG. 26, the display of color may be changed according to the lesion evaluation value to be displayed as a heat map. In the lesion evaluation value 172a of FIG. 26, a height of the lesion evaluation value is indicated by a height of a hatching line density (a region 172b with a high lesion evaluation value, a region 172c with a medium lesion evaluation value, a region 172d with a low lesion evaluation value, and a normal region 172e with an extremely low lesion evaluation value). In the superimposed image 173 illustrated in FIG. 26, the lesion evaluation value 172a is superimposed on the display image 171. In FIG. 26, a difference in the lesion evaluation value is indicated by a difference in the density of the hatching lines, but is actually displayed with a difference in a density of the color. In a case where the lesion evaluation value is displayed in color, for example, a region with a high lesion evaluation value may be displayed in red, a region with a medium lesion evaluation value may be displayed in yellow, and a region with a low lesion evaluation value may be displayed in blue. With the above configuration, it is possible to simply find a location with a high degree of lesion, and to reduce a burden of diagnosis on a user in a case where it is necessary to observe many images.

It is preferable that in a case where the superimposed image is generated, the display image is the first illumination light image, and the input image to which the lesion evaluation value is output is the second illumination light image. The first illumination light image is an endoscopic image illuminated with white light and is an image normally familiar to a doctor. On the other hand, the second illumination light image is an endoscopic image which is illuminated with special light and in which blood vessels are enhanced, but is an image that requires training for accurate interpretation. Therefore, the user can check the lesion evaluation value on the first illumination light image by outputting the lesion evaluation value on the second illumination light image with which a lesion can be determined with higher accuracy and superimposing the lesion evaluation value on the first illumination light image of a frame immediately after the output of the lesion evaluation value.

Figure 27:
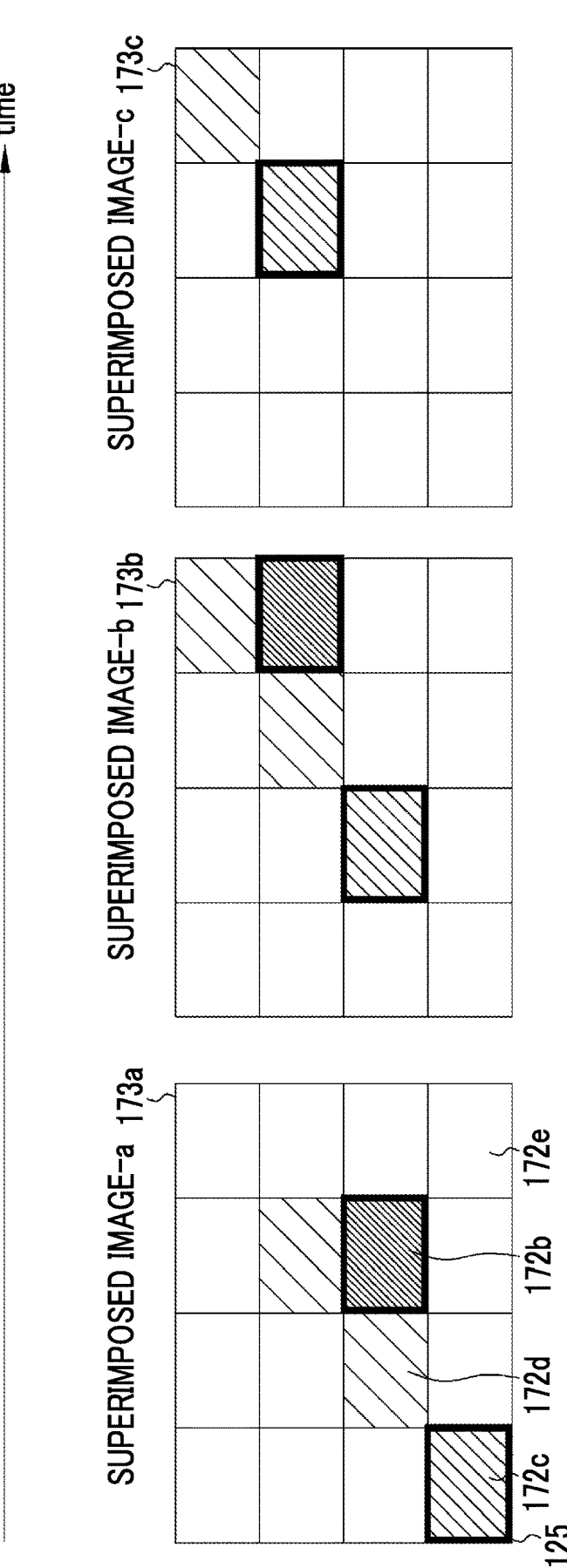
FIG. 27 is an image diagram illustrating an example in which a plurality of superimposed images are arranged and displayed in a time-series order.

Further, a plurality of superimposed images may be arranged and displayed in a time-series order as illustrated in FIG. 27. In this case, the frame 125 may be provided and displayed in a region where the lesion evaluation value is high such that a region where the lesion evaluation value is high to some extent can be seen along a time series. In the specific examples of FIG. 27, images are acquired in the order of a superimposed image-a 173a, a superimposed image-b 173b, and a superimposed image-c 173c, and the lesion evaluation values of the images are illustrated (the region 172b with a high lesion evaluation value, the region 172c with a medium lesion evaluation value, the region 172d with a low lesion evaluation value, and the normal region 172e with an extremely low lesion evaluation value). Among these regions, the frames 125 are added to the region 172b with a high lesion evaluation value and the region 172c with a medium lesion evaluation value. In addition, each region of interest may be displayed with a number or a symbol. With the above configuration, it is possible to display a plurality of images while performing registration of a region with a high lesion degree between the plurality of images, and to easily find the same lesion area on images obtained in a time-series order.

A display method in a case where the display 17 includes a first display 17a and a second display 17b, and the first display 17a and the second display 17b are electrically connected to the processor device 15 will be described. As illustrated in FIG. 28, the display image may be displayed on a first screen 180 of the first display 17a, and an image to which the lesion evaluation value is output may be displayed on a second screen 182 of the second display 17b. As illustrated in FIG. 28, in a case where the display image and the lesion evaluation value are displayed using the first screen and the second screen, it is preferable that the display image displayed on the first screen is the first illumination light image and the image to which the lesion evaluation value displayed on the second screen is output is the second illumination light image of the frame immediately before the display image. The display image may be displayed on the first screen and the superimposed image may be displayed on the second screen. The superimposed image may be displayed on the first screen and the image to which the lesion evaluation value is output may be displayed on the second screen. In addition, a third screen may be provided to simultaneously display the display image, the image to which the lesion evaluation value is output, and the superimposed image.

Figure 29:
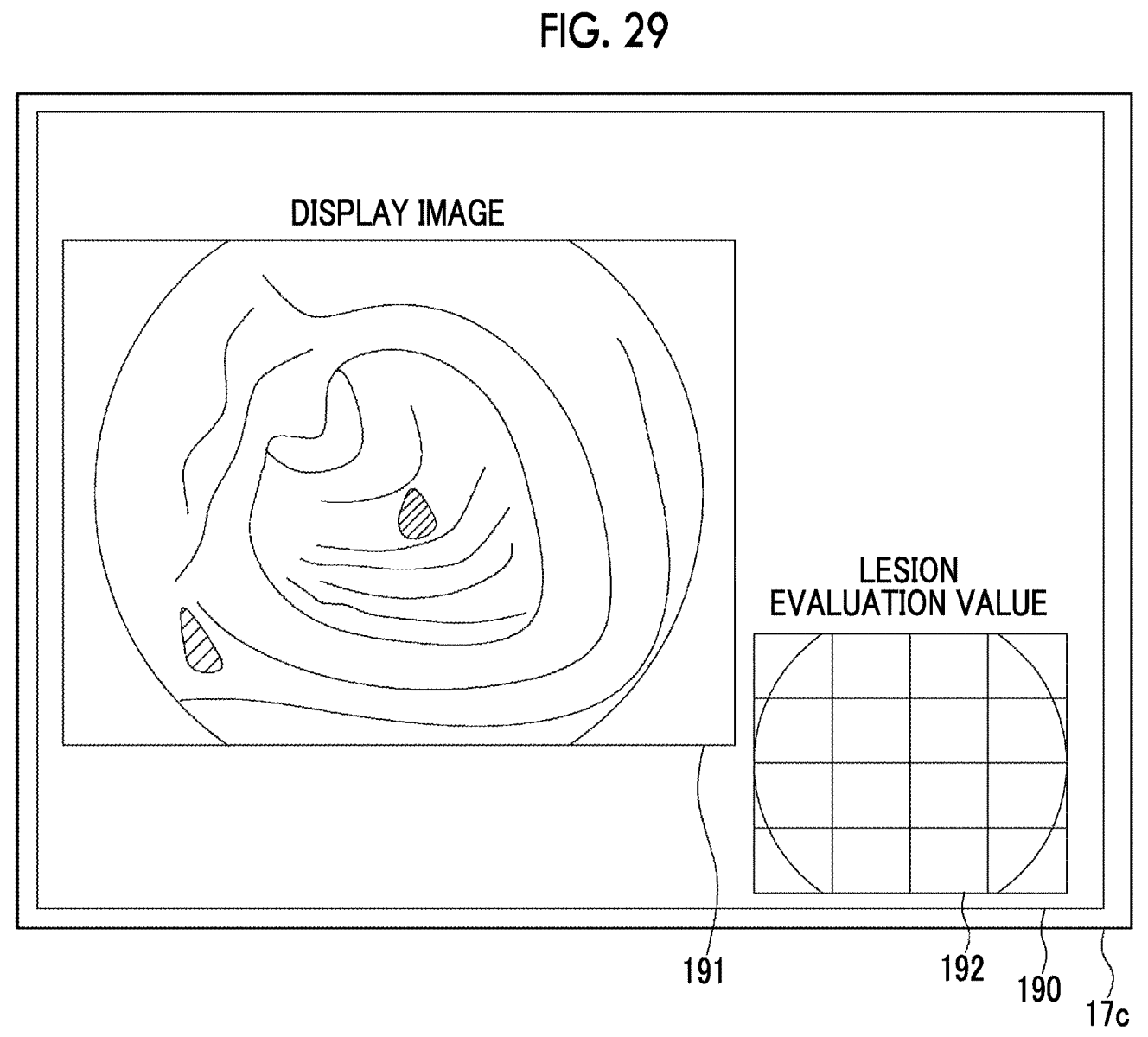

A display method in a case where the display 17 has only one specific display 17c will be described. As illustrated in FIG. 29, a display image 191 as the first screen 180 and an input image 192, to which the lesion evaluation value is output, as the second screen 182 may be displayed as one display screen 190 on the specific display 17c. Even in a case where the display screen 190 is displayed on the specific display 17c, it is preferable that the display image is the first illumination light image and the image to which the lesion evaluation value is output is the second illumination light image of the frame immediately before the display image. Any two or more of the display image, the image to which the lesion evaluation value is output, and the superimposed image may be displayed on the specific display 17c. In a case where two or more of any of the display image, the image to which the lesion evaluation value is output, and the superimposed image are displayed on the specific display 17c, the display size may be changed. For example, as illustrated in FIG. 29, in a case where two or more images including the display image are displayed, the display image may be displayed in a larger size than other images. The input image 192 to which the lesion evaluation value is output in the specific example of FIG. 29 may display the lesion evaluation value as a numerical value as illustrated in FIG. 28, or may display the lesion evaluation value in color. With the above-described configuration, the display image or the superimposed image can be compared with the image used for the image analysis.

Figure 30:
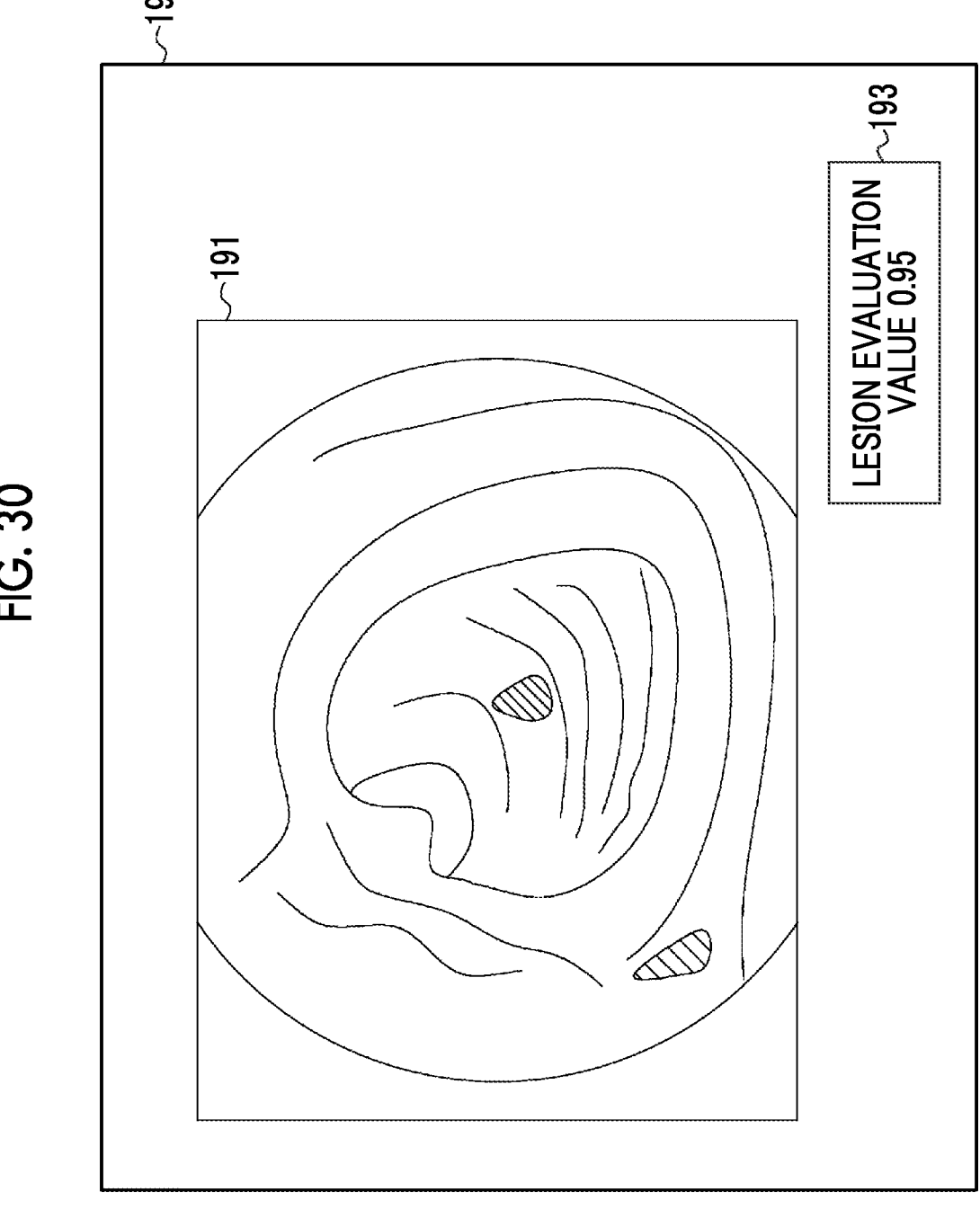
FIG. 30 is an image diagram illustrating an example in which the display image and the lesion evaluation value output for the entire image are displayed on the display screen.

As illustrated in FIG. 30, in a case where the lesion evaluation value for the entire divided input image is output, the display image 191 and a lesion evaluation value 193 may be displayed on one display screen 190.

Figure 31:
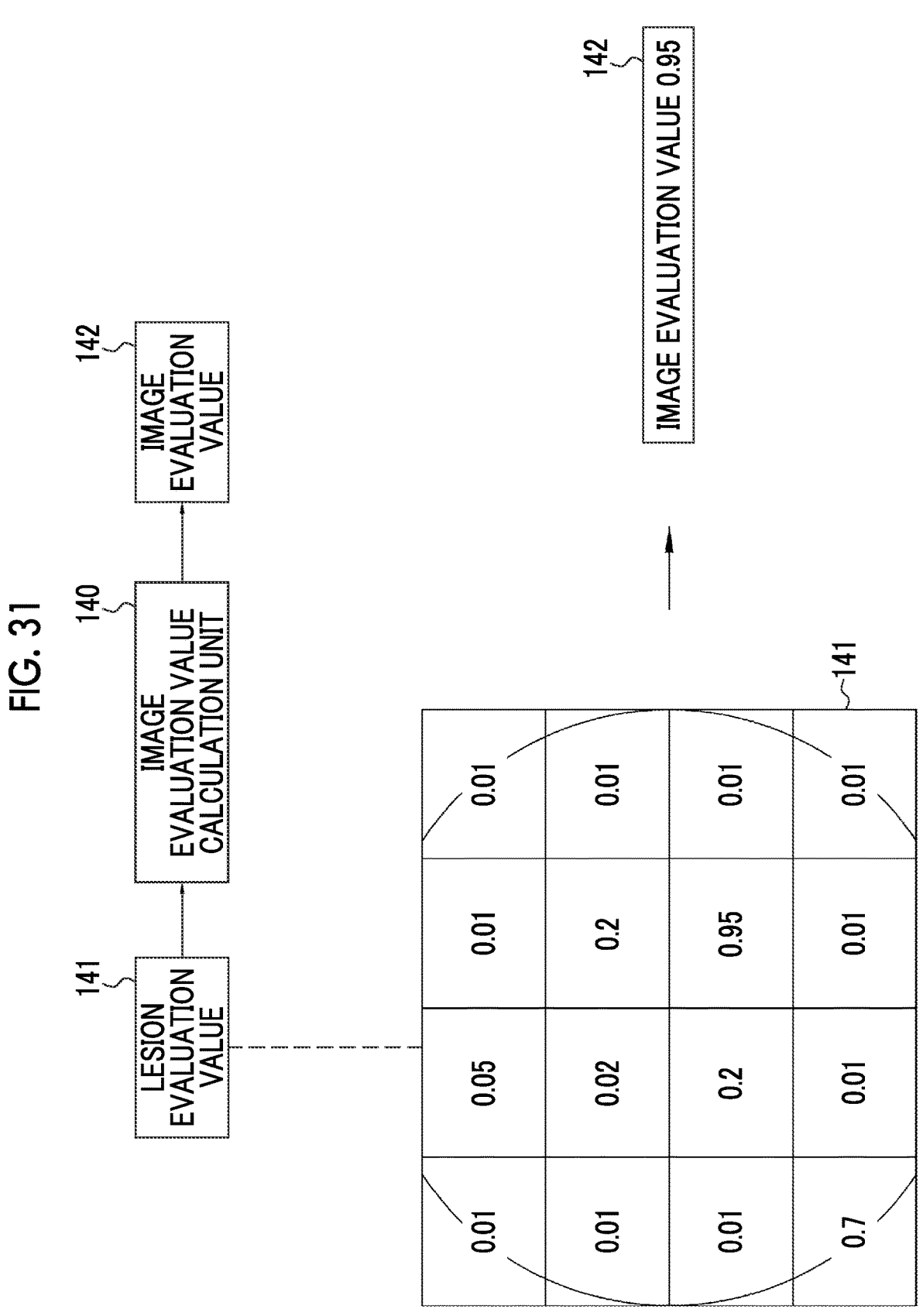
FIG. 31 is an explanatory diagram illustrating an example of calculation of an image evaluation value.

In a case where the second classifier 120 outputs the lesion evaluation value for each region of the input image or the removal image divided into a plurality of regions, the image evaluation value for the input image of any one frame may be calculated using lesion evaluation values added to the plurality of regions. The input image or the removal image in which the lesion evaluation value is added to each region is transmitted to the image evaluation value calculation unit 140, and the image evaluation value is calculated. The image evaluation value may be an average or a sum of the lesion evaluation values added to the respective regions of the input image or the removal image, and as in an example of calculation of the image evaluation value illustrated in FIG. 31, the highest lesion evaluation value among the lesion evaluation values 141 added to the respective regions may be set as an image evaluation value 142.

Furthermore, a site evaluation value for input images of a plurality of frames may be calculated using the lesion evaluation value added to the input image or the removal image divided into a plurality of regions of a plurality of frames. The input images or the removal images of the plurality of frames in which the lesion evaluation value is added to each region are transmitted to the site evaluation value calculation unit 150 and the site evaluation value is calculated. The site evaluation value is obtained for the input images or the removal images of a plurality of frames obtained at each of large intestine sites, such as the rectum, the sigmoid colon, the descending colon, the transverse colon, and the ascending colon. The input images of the plurality of frames transmitted to the site evaluation value calculation unit 150 may be arbitrarily selected by the user. That is, the "site" for which the site evaluation value is calculated may be set by any method of the user. In addition, the computer 16 may automatically recognize anatomical sites, such as the rectum, the sigmoid colon, the descending colon, the transverse colon, and the ascending colon, from the examination image (input image or removal image), and the site evaluation value calculation unit 150 may calculate a site evaluation value corresponding to each site from the lesion evaluation value added to the input image or the removal image of a frame corresponding to each site.

Figure 32:
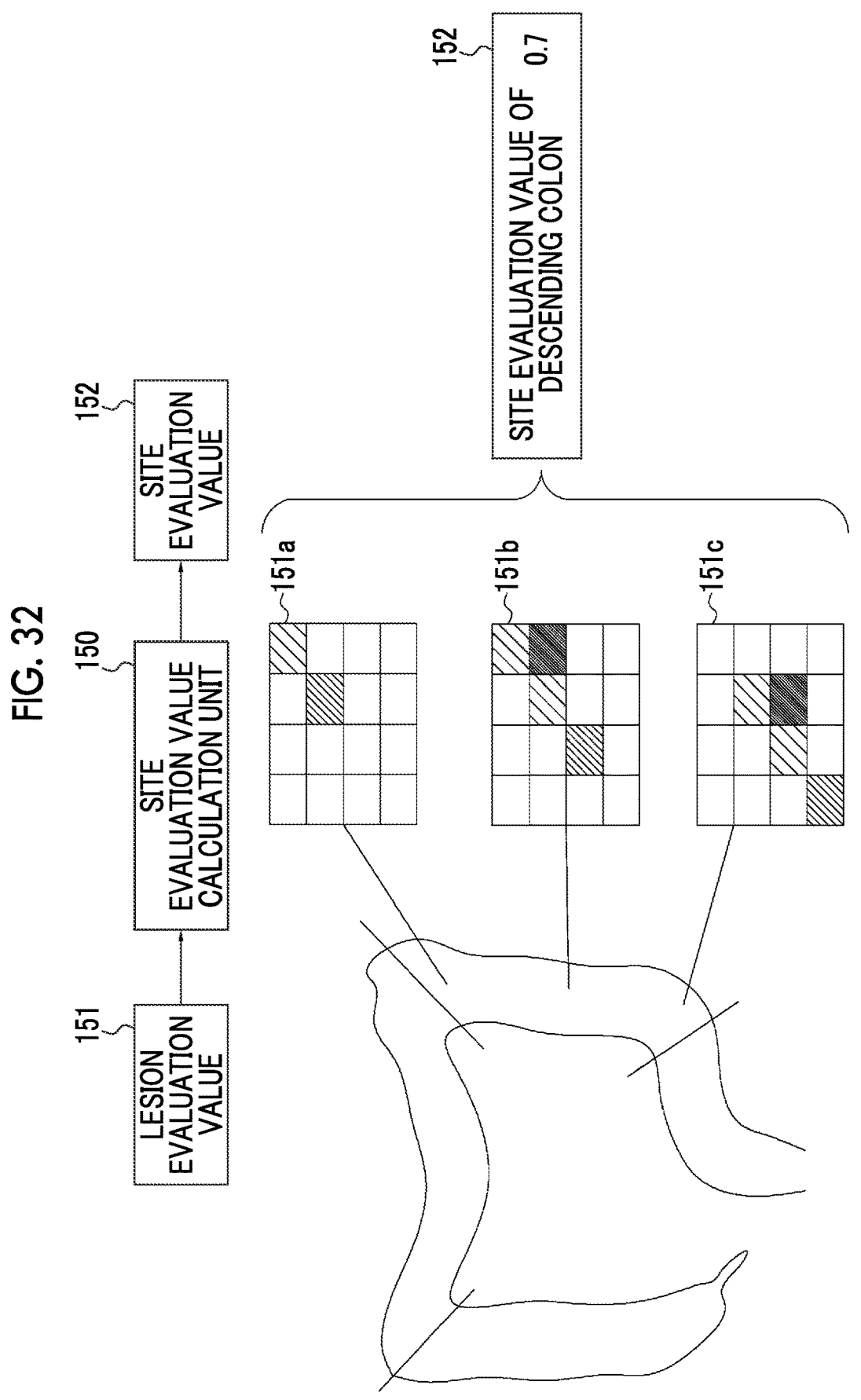
FIG. 32 is an explanatory diagram illustrating an example of calculation of a site evaluation value.

The site evaluation value is an average or a sum of the lesion evaluation values added to the respective regions of the input images of a plurality of frames. In addition, the average or the sum of the image evaluation values may be used as the site evaluation value, or the highest image evaluation value among the set sites may be used as the site evaluation value. An example of calculation of the site evaluation value illustrated in FIG. 32 will be described. Images 151a, 151b, and 151c in FIG. 32 are images in which the lesion evaluation values are obtained and which are arranged in a time-series order (in a case where the endoscope 12 is inserted from the anal portion and an examination is performed, the image 151c, the image 151b, and the image 151a are acquired in this order). In the images 151a, 151b, and 151c in FIG. 32, the height of the lesion evaluation value is indicated by the height of the density of the hatching lines. The lesion evaluation values 151 of the image 151a, the image 151b, and the image 151c acquired in the respective regions in the descending colon are transmitted to the site evaluation value calculation unit 150, and are averaged to obtain a site evaluation value 152 of one site (descending colon in FIG. 32). In an example of FIG. 32, since the site evaluation value is calculated for the descending colon, the site evaluation value 152 may be used as a descending colon evaluation value. Similarly, a rectum evaluation value, a sigmoid colon evaluation value, a transverse colon evaluation value, an ascending colon evaluation value, and the like may be calculated.

In addition, an overall evaluation value may be calculated using the lesion evaluation value added to the input image or the removal image divided into a plurality of regions of all the frames acquired during the examination. The input image or the removal image in which the lesion evaluation value is added to each region is transmitted to the overall evaluation value calculation unit 160, and the overall evaluation value is calculated. The overall evaluation value may be calculated using the image evaluation value or the site evaluation value.

Figure 33:
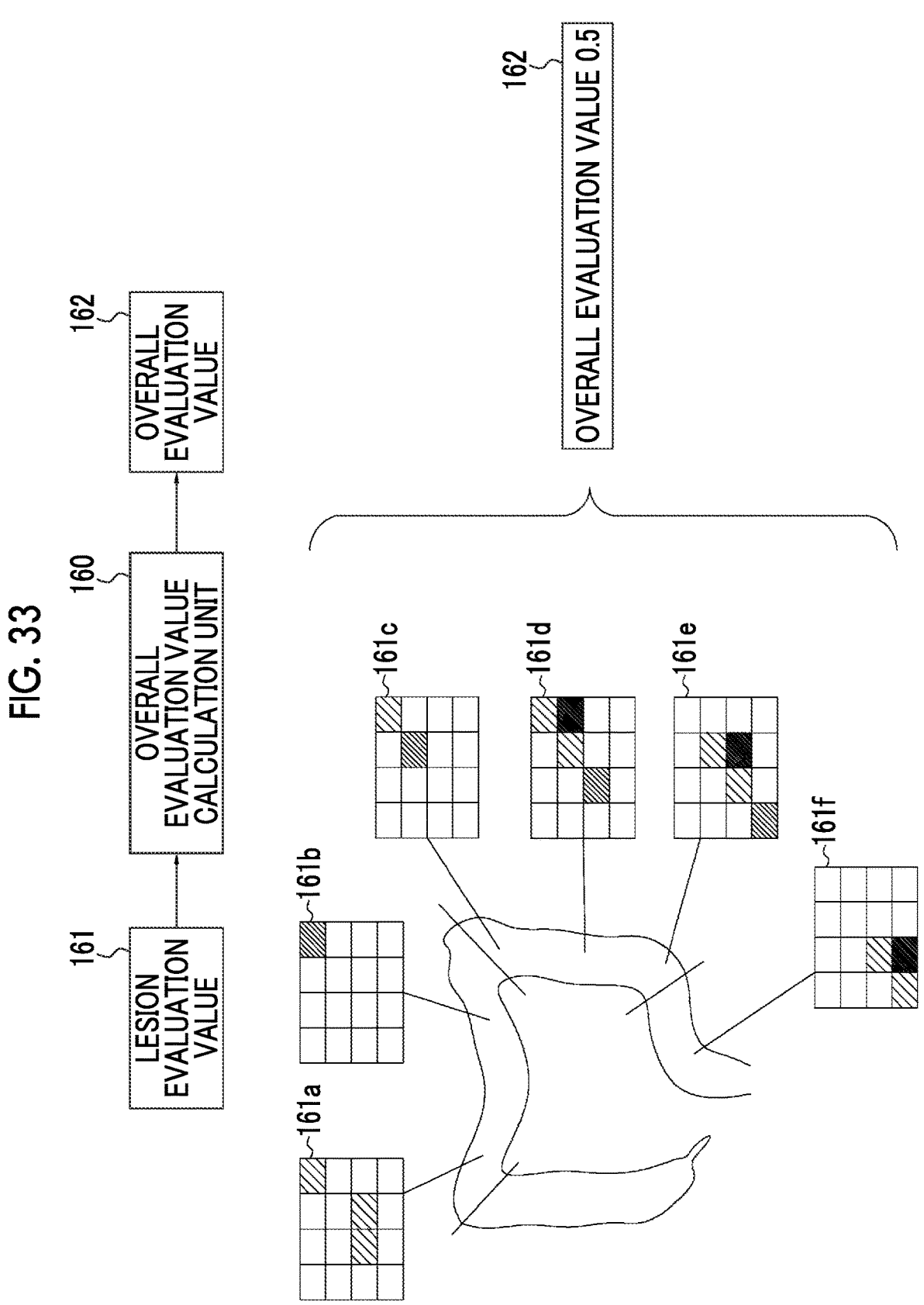
FIG. 33 is an explanatory diagram illustrating an example of calculation of an overall evaluation value.

An example of calculation of the overall evaluation value illustrated in FIG. 33 will be described. Images 161a, 161b, 161c, 161d, 161e, and 161f in FIG. 33 are images in which the lesion evaluation values are obtained and which are arranged in a time-series order (in a case where the endoscope 12 is inserted from the anal portion and examination is performed, the image 161*f*, the image 161*e*, the image 161*d*, the image 161*c*, the image 161*b*, and the image 161*a* are acquired in this order). In the images 161*a* to 161*f* in FIG. 33, the height of the lesion evaluation value is indicated by the height of the density of the hatching lines. The lesion evaluation values 161 calculated in the images 161*a* to 161*f* are transmitted to the overall evaluation value calculation unit 160 and averaged to obtain an overall evaluation value 162 of one site (descending colon in FIG. 32). In addition, a transverse colon evaluation value may be calculated from the image 161*a* and the image 161*b*, a descending colon evaluation value may be calculated from the image 161*c*, the image 161*d*, and the image 161*e*, a sigmoid colon evaluation value may be calculated from the image 161*f*, and the overall evaluation value 162 may be calculated using the transverse colon evaluation value, the descending colon evaluation value, and the sigmoid colon evaluation value.

Figure 34:
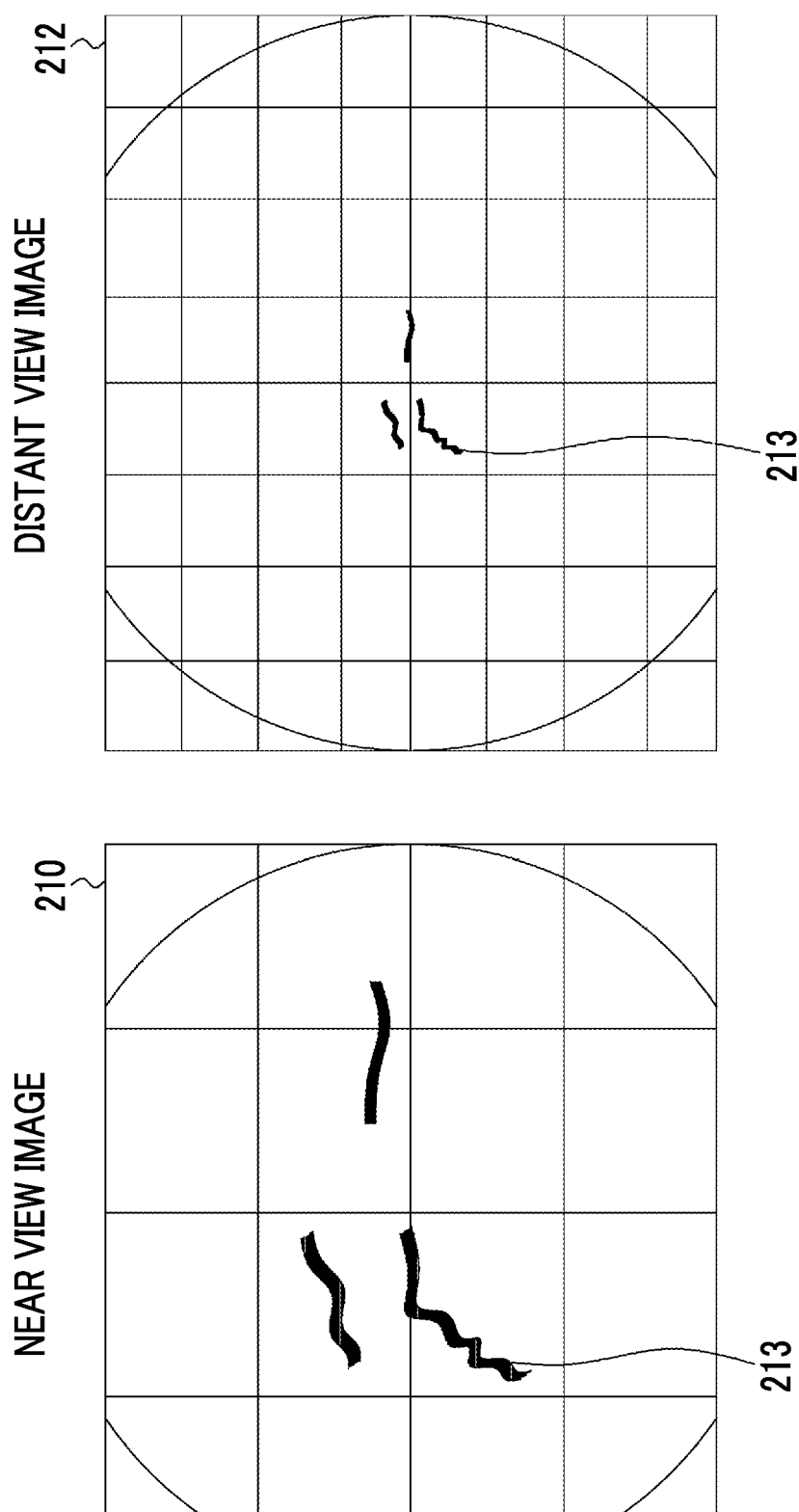
FIG. 34 is an explanatory diagram illustrating a method of dividing each region of a near view image and a distant view image.

It is preferable that the image division unit 100 determines a shape, a size, and/or the number of divisions of the input image based on a magnification at which the examination image is acquired. For example, as illustrated in FIG. 34, in accordance with a size of the blood vessel 213, the number of divisions and a division size are set to be large in a near view image 210 having a high observation magnification, and the number of divisions and the division size are set to be small in a distant view image 212 having a low observation magnification. In a case where the observation magnification is high, since an area occupied by the region of interest or the evaluation inhibition target in the input image is large, it is preferable to make each divided region larger. On the other hand, in a case where the observation magnification is low, since the area occupied by the region of interest or the evaluation inhibition target in the input image is small, an evaluation accuracy can be improved by making each divided region smaller. The shape, size, and/or number of divisions in the same image may be changed, such as increasing the number of divisions at an edge of a screen where the blurriness or distortion is likely to occur and decreasing the number of divisions at a center of an image that can be easily focused.

In the present embodiment, an example in which the processor device 15 and the computer 16 are provided in the endoscope system 10 has been described. However, the present invention is not limited thereto, and other medical devices may be used. As the endoscope 12, a rigid endoscope or a flexible endoscope may be used. In addition, a part or all of the examination image acquisition unit 60 and/or the central control unit 55 of the endoscope system 10 can be provided in, for example, a medical image processing device that communicates with the processor device 15 and cooperates with the endoscope system 10. For example, they can be provided in a diagnosis support device that acquires an image captured by the endoscope 12 directly from the endoscope system 10 or indirectly from a PACS. Further, a medical service support device that is connected to various examination devices, such as a first examination device, a second examination device, . . . , and an N-th examination device, including the endoscope system 10, through a network can be provided with a part or all of the image acquisition unit 50 and/or the control unit 30 of the endoscope system 10.

In the present embodiment, hardware structures of processing units that execute various kinds of processing, such as the image acquisition unit 50, the digital signal processor (DSP) 52, the noise reduction unit 53, the image processing switching unit 54, the examination image acquisition unit 60, the image selection unit 90, the display control unit 200, the image input unit 92, the image division unit 100, the first classifier 110, the second classifier 120, the third classifier 130, the image evaluation value calculation unit 140, the site evaluation value calculation unit 150, and the overall evaluation value calculation unit 160, are various processors as indicated below. The various processors include a central processing unit (CPU) that is a general-purpose processor functioning as various processing units by executing software (program), a programmable logic device (PLD) that is a processor of which a circuit configuration can be changed after manufacturing such as a field programmable gate array (FPGA), a dedicated electric circuit that is a processor having a circuit configuration exclusively designed to execute various types of processing, and the like.

One processing unit may be configured by one of the various processors, or a combination of two or more processors of the same type or different types (for example, a combination of a plurality of FPGAs or a combination of a CPU and an FPGA). In addition, a plurality of processing units may be configured by one processor. As an example of configuring a plurality of processing units with one processor, first, there is a form in which, as typified by computers such as a client and a server, one processor is configured by combining one or more CPUs and software, and the processor functions as a plurality of processing units. Second, there is a form in which, as typified by a system on chip (SoC) and the like, a processor that implements functions of an entire system including a plurality of processing units with one integrated circuit (IC) chip is used. As described above, the various processing units are configured using one or more of the various processors as a hardware structure.

Furthermore, the hardware structures of these various processors are more specifically electrical circuitry in a form in which circuit elements, such as semiconductor elements, are combined. A hardware structure of the storage unit is a storage device such as a hard disc drive (HDD) or a solid state drive (SSD).

EXPLANATION OF REFERENCES

10: endoscope system
12: endoscope
12*a*: insertion portion
12*b*: operation portion
12*c*: bendable portion
12*d*: distal end portion
12*e*: angle knob
12*f*: observation mode selector switch
12*g*: image analysis mode selector switch
12*h*: still image acquisition instruction switch
12*i*: zoom operation portion
14: light source device
15: processor device
16: computer
17: display
17*a*: first display
17*b*: second display
17*c*: specific display
19: user interface
20: light source unit
20*a*: V-LED
20*b*: B-LED
20*c*: G-LED
20*d*: R-LED
21: light source processor 22: optical path coupling unit
23: light guide
30a: illumination optical system
30b: imaging optical system
31: illumination lens
41: objective lens
42: zoom lens
43: imaging sensor
44: imaging processor
45: CDS/AGC circuit
46: A/D converter
50: image acquisition unit
52: DSP
53: noise reduction unit
54: image processing switching unit
55: central control unit
60: examination image acquisition unit
70: first illumination light image generation unit
80: second illumination light image generation unit
90: image selection unit
92: image input unit
100: image division unit
101: pool portion
102: divided input image
103: reflection
104a: edge portion of cap
104b: entire cap region including edge portion of cap
106: image peripheral portion
107: bubbles
110: first classifier
112: region evaluation value
120: second classifier
121: input image to which region evaluation value is added
122: lesion evaluation value
124: extraction region
125: frame
126: region of interest
130: third classifier
131: input image
132: removal image
140: image evaluation value calculation unit
141: lesion evaluation value of example in FIG. 31
142: image evaluation value
150: site evaluation value calculation unit
151: lesion evaluation value of example in FIG. 32
151a, 151b, 151c: image to which lesion evaluation value is output in FIG. 32
152: site evaluation value
160: overall evaluation value calculation unit
161: lesion evaluation value
161a, 161b, 161c, 161d, 161e, 161f: input image of example in FIG. 33
162: overall evaluation value
171: display image
172: examination image of frame immediately before display image
172a: lesion evaluation value
172b: region with high lesion evaluation value
172c: region with medium lesion evaluation value
172d: region with low lesion evaluation value
172e: normal region with extremely low lesion evaluation value
173: superimposed image
173a: superimposed image-a
173b: superimposed image-b
173c: superimposed image-c 180: first screen
182: second screen
190: display screen
191: display image
192: input image to which lesion evaluation value is output
193: lesion evaluation value
200: display control unit
210: near view image
212: distant view image
213: blood vessel

What is claimed is:

1. An endoscope system that illuminates a subject and captures light from the subject, the endoscope system comprising:
an endoscope; and
an image control processor configured to:
acquire an examination image based on an image signal captured by the endoscope;
divide the examination image into a plurality of regions as an input image;
input the input image divided into the plurality of predetermined regions to a first classifier to output region evaluation values for the plurality of regions, wherein the first classifier is trained by machine learning and configured to detect an evaluation inhibition target which is a structure or an artifact not suitable for outputting a lesion evaluation value by outputting an region evaluation value for each of the plurality of regions, as a region of the plurality of regions having the evaluation inhibition target has a lower region evaluation value than a region not having the evaluation inhibition target; and
input the input image in which the region evaluation values are added to the plurality of regions to a second classifier which is trained by machine learning and configured to evaluate a presence of a lesion in each region of the plurality of regions to output a lesion evaluation value for each region of the plurality of regions as a region of the plurality of regions having detected the presence of the lesion has a higher lesion evaluation value than a region not having detected the presence of the lesion.

2. The endoscope system according to claim 1, wherein the image control processor is configured to input the input image consisting of an extraction region extracted based on the region evaluation value among the plurality of regions to the second classifier to output the lesion evaluation value.

3. The endoscope system according to claim 1, wherein the region evaluation value is a value obtained by digitizing presence or absence of the evaluation inhibition target that is not suitable for outputting the lesion evaluation value on the input image and decreases an output accuracy of the lesion evaluation value and an influence of the evaluation inhibition target on the output of the lesion evaluation value.

4. The endoscope system according to claim 2, wherein the image control processor is configured to set the plurality of regions in which the region evaluation value is equal to or greater than a threshold value as the extraction region.

5. The endoscope system according to claim 4, wherein the plurality of regions in which the region evaluation value is less than the threshold value are regions including any one of a puddle, a blood pool, a liquid pool, a bubble, a distortion, blurriness, a reflection, or a cap.

6. The endoscope system according to claim 1, further comprising:
a light source processor configured to:
control emission of first illumination light and second illumination light having emission spectra different from each other, and
emit the first illumination light in a first emission pattern and emit the second illumination light in a second emission pattern in a case where a first illumination period during which the first illumination light is emitted and a second illumination period during which the second illumination light is emitted are automatically switched, and
wherein the image control processor is configured to set a first illumination light image based on the first illumination light or a second illumination light image based on the second illumination light as the input image.

7. The endoscope system according to claim 6,
wherein the image control processor is configured to set the second illumination light image as the input image.

8. The endoscope system according to claim 6,
wherein the first illumination light is white light, and the second illumination light is light having a peak wavelength of 410 nm±10.

9. The endoscope system according to claim 6, further comprising a display,
wherein the image control processor is configured to superimpose the lesion evaluation value output based on the second illumination light image acquired in a frame immediately before the first illumination light image is acquired as a numerical value or a color on the first illumination light image and display a superimposed image on the display.

10. The endoscope system according to claim 9,
wherein the image control processor is configured to perform any one of:
displaying the first illumination light image on a first screen of a first display and displaying the lesion evaluation value output based on the second illumination light image acquired in the frame immediately before the first illumination light image is acquired on a second screen of a second display in a case where the display comprises the first display and the second display different from each other; or
displaying the first illumination light image on a first screen of a specific display and displaying the lesion evaluation value on a second screen of the specific display in a case where the display includes only one specific display.

11. The endoscope system according to claim 6,
wherein the first emission pattern is any one of a first A emission pattern in which the number of frames of the first illumination period is the same in each of the first illumination periods or a first B emission pattern in which the number of frames of the first illumination period is different in each of the first illumination periods.

12. The endoscope system according to claim 6,
wherein the second emission pattern is any one of:
a second A pattern in which the number of frames of the second illumination period is the same in each of the second illumination periods, and an emission spectrum of the second illumination light is the same in each of the second illumination periods;
a second B pattern in which the number of frames of the second illumination period is the same in each of the second illumination periods, and an emission spectrum of the second illumination light is different in each of the second illumination periods;
a second C pattern in which the number of frames of the second illumination period is different in each of the second illumination periods, and an emission spectrum of the second illumination light is the same in each of the second illumination periods; or
a second D pattern in which the number of frames of the second illumination period is different in each of the second illumination periods, and an emission spectrum of the second illumination light is different in each of the second illumination periods.

13. The endoscope system according to claim 6,
wherein the image control processor is configured to:
calculate an image evaluation value for the input image of any one frame using the lesion evaluation values for the plurality of regions output based on the input image of the one frame;
calculate site evaluation values for the input images of a plurality of frames using the lesion evaluation values for the plurality of regions output based on the input images of the plurality of frames; and
calculate an overall evaluation value using the image evaluation values and/or the site evaluation values added to the input images of all the frames to which the lesion evaluation values are output.

14. The endoscope system according to claim 1,
wherein the image control processor is configured to determine a shape, a size, and/or the number of divisions of the input image based on a magnification at which the examination image is acquired.

15. The endoscope system according to claim 1,
wherein the lesion evaluation value is output based on an evaluation index for ulcerative colitis.

16. A method of operating an endoscope system provided with an endoscope that illuminates a subject and captures light from the subject and an image control processor, the method comprising steps, executed by the image control processor, of:
acquiring an examination image based on an image signal captured by the endoscope;
dividing the examination image into a plurality of regions as an input image;
inputting the input image divided into the plurality of predetermined regions to a first classifier to output region evaluation values for the plurality of regions, wherein the first classifier is trained by machine learning and configured to detect an evaluation inhibition target which is a structure or an artifact not suitable for outputting a lesion evaluation value by outputting an region evaluation value for each of the plurality of regions, as a region of the plurality of regions having the evaluation inhibition target has a lower region evaluation value than a region not having the evaluation inhibition target; and
inputting the input image in which the region evaluation values are added to the plurality of regions to a second classifier which is trained by machine learning and configured to evaluate a presence of a lesion in each region of the plurality of regions to output a lesion evaluation value for each region of the plurality of regions as a region of the plurality of regions having detected the presence of the lesion has a higher lesion evaluation value than a region not having detected the presence of the lesion.

*   *   *   *   *